US011648279B2

(12) United States Patent
Yoshida et al.

(10) Patent No.: US 11,648,279 B2
(45) Date of Patent: May 16, 2023

(54) COMPOSITION FOR CELL TRANSPLANT, AND METHOD FOR CELL TRANSPLANT

(71) Applicants: KYOTO UNIVERSITY, Kyoto (JP); SANYO CHEMICAL INDUSTRIES, LTD., Kyoto (JP)

(72) Inventors: Yoshinori Yoshida, Kyoto (JP); Takeshi Hatani, Kyoto (JP); Ryosuke Suzuki, Kyoto (JP); Shingo Kawabata, Kyoto (JP)

(73) Assignees: KYOTO UNIVERSITY, Kyoto (JP); SANYO CHEMICAL INDUSTRIES, LTD., Kyoto (JP)

( * ) Notice: Subject to any disclaimer, the term of this patent is extended or adjusted under 35 U.S.C. 154(b) by 255 days.

(21) Appl. No.: 16/973,625

(22) PCT Filed: May 9, 2019

(86) PCT No.: PCT/JP2019/018606
§ 371 (c)(1),
(2) Date: Dec. 9, 2020

(87) PCT Pub. No.: WO2019/239751
PCT Pub. Date: Dec. 19, 2019

(65) Prior Publication Data
US 2021/0252074 A1    Aug. 19, 2021

(30) Foreign Application Priority Data
Jun. 12, 2018 (JP) .............................. JP2018-111976

(51) Int. Cl.
*A61K 35/34* (2015.01)
*A61K 38/16* (2006.01)

(52) U.S. Cl.
CPC ............ *A61K 35/34* (2013.01); *A61K 38/164* (2013.01)

(58) Field of Classification Search
None
See application file for complete search history.

(56) References Cited

U.S. PATENT DOCUMENTS

2007/0092492 A1    4/2007    Matsuda et al.

FOREIGN PATENT DOCUMENTS

| JP | 2002-145797 | 5/2002 |
|----|-------------|--------|
| JP | 2007-528755 | 10/2007 |
| JP | 2018-861 | 1/2018 |
| WO | 2012/172887 | 12/2012 |

OTHER PUBLICATIONS

Shenje et al., "Lineage tracing of cardiac explant derived cells", PLoS One Apr. 16; 3(4): e1929 doi: 10.1371/journal.pone.0001929 (Year: 2008).*
Majid et al., "Natural Biomaterials for Cardiac Tissue Engineering: A Highly Biocompatible Solution", Front. Cardivasc. Med. 7: 554597 pp. 1-32 October (Year: 2020).*
Chaudhuri et al., "Biomaterials and cells for cardiac tissue engineering: Current choices", Materials Science and Engineering C 79: 950-957 (Year: 2017).*
International Search Report dated Jul. 16, 2019 in International (PCT) Application No. PCT/JP2019/018606.
Suzuki et al., "Targeted Cell Delivery Into Infarcted Rat Hearts by Retrograde Intracoronary Infusion: Distribution, Dynamics, and Influence on Cardiac Function", Circulation, Sep. 14, 2004, pp. II-225 to II-230.

* cited by examiner

*Primary Examiner* — Anand U Desai
(74) *Attorney, Agent, or Firm* — Wenderoth, Lind & Ponack, L.L.P.

(57) ABSTRACT

Provided are a composition for cell transplant and a method for cell transplant, both of which enable a myocardial tissue to favorably retain cardiac myocytes and/or cardiac progenitors and can improve the persistence and proliferation of transplanted cells. The composition for cell transplant of the present invention is a composition for cell transplant, containing cells and an aqueous solution containing a protein (A), the cells including a cardiac myocyte and/or a cardiac progenitor, the protein (A) having a degree of hydrophobicity of 0.2 to 1.2, the protein (A) containing a polypeptide chain (Y) and/or a polypeptide chain (Y'), the protein (A) containing 1 to 100 polypeptide chains as a total of the polypeptide chain (Y) and the polypeptide chain (Y'), the polypeptide chain (Y) being a polypeptide chain having 2 to 100 continuous amino acid sequences (X), the amino acid sequence (X) having any one of a VPGVG sequence (1) corresponding to an amino acid sequence of SEQ ID NO: 1, a GVGVP sequence (2) corresponding to an amino acid sequence of SEQ ID NO: 2, a GPP sequence, a GAP sequence, and a GAHGPAGPK sequence (3) corresponding to an amino acid sequence of SEQ ID NO: 3, the polypeptide chain (Y') being a polypeptide chain having a structure in which 0.1 to 5% amino acid residues in the polypeptide chain (Y) are replaced by a lysine residue and/or an arginine residue and including 1 to 100 residues as a total of the lysine residue and the arginine residue.

8 Claims, No Drawings

Specification includes a Sequence Listing.

```
                       SEQUENCE LISTING

<160> NUMBER OF SEQ ID NOS: 19

<210> SEQ ID NO 1
    <211> LENGTH: 5
    <212> TYPE: PRT
    <213> ORGANISM: Homo sapiens

<400> SEQUENCE: 1

Val Pro Gly Val Gly
    1               5

<210> SEQ ID NO 2
    <211> LENGTH: 5
    <212> TYPE: PRT
    <213> ORGANISM: Homo sapiens

<400> SEQUENCE: 2

Gly Val Gly Val Pro
    1               5

<210> SEQ ID NO 3
    <211> LENGTH: 9
    <212> TYPE: PRT
    <213> ORGANISM: Artificial sequence
    <220> FEATURE:
    <223> OTHER INFORMATION: Amino acid sequence(X)

<400> SEQUENCE: 3

Gly Ala His Gly Pro Ala Gly Pro Lys
    1               5

<210> SEQ ID NO 4
    <211> LENGTH: 6
    <212> TYPE: PRT
    <213> ORGANISM: Artificial sequence
    <220> FEATURE:
    <223> OTHER INFORMATION: Amino acid sequence

<400> SEQUENCE: 4

Gly Ala Gly Ala Gly Ser
    1               5

<210> SEQ ID NO 5
    <211> LENGTH: 24
    <212> TYPE: PRT
    <213> ORGANISM: Artificial sequence
    <220> FEATURE:
    <223> OTHER INFORMATION: Polypeptide chain(S)

<400> SEQUENCE: 5

Gly Ala Gly Ala Gly Ser Gly Ala Gly Ala Gly Ser Gly Ala Gly Ala
    1               5                   10                  15
```

Gly Ser Gly Ala Gly Ala Gly Ser
            20

<210> SEQ ID NO 6
<211> LENGTH: 40
<212> TYPE: PRT
<213> ORGANISM: Artificial sequence
<220> FEATURE:
<223> OTHER INFORMATION: Polypeptide chain(X')

<400> SEQUENCE: 6

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro
        35                  40

<210> SEQ ID NO 7
<211> LENGTH: 5
<212> TYPE: PRT
<213> ORGANISM: Artificial sequence
<220> FEATURE:
<223> OTHER INFORMATION: Amino acid sequence(X')

<400> SEQUENCE: 7

Gly Lys Gly Val Pro
1               5

<210> SEQ ID NO 8
<211> LENGTH: 5
<212> TYPE: PRT
<213> ORGANISM: Artificial sequence
<220> FEATURE:
<223> OTHER INFORMATION: Amino acid sequence(X')

<400> SEQUENCE: 8

Gly Lys Gly Lys Pro
1               5

<210> SEQ ID NO 9
<211> LENGTH: 5
<212> TYPE: PRT
<213> ORGANISM: Artificial sequence
<220> FEATURE:
<223> OTHER INFORMATION: Amino acid sequence(X')

<400> SEQUENCE: 9

Gly Lys Gly Arg Pro
1               5

<210> SEQ ID NO 10
<211> LENGTH: 5
<212> TYPE: PRT
<213> ORGANISM: Artificial sequence
<220> FEATURE:
<223> OTHER INFORMATION: Amino acid sequence(X')

<400> SEQUENCE: 10

Gly Arg Gly Arg Pro
1               5

<210> SEQ ID NO 11
<211> LENGTH: 5
<212> TYPE: PRT

```
<213> ORGANISM: Artificial sequence
<220> FEATURE:
<223> OTHER INFORMATION: Amino acid sequence(Z)

<400> SEQUENCE: 11

Val Ala Ala Gly Tyr
1               5

<210> SEQ ID NO 12
<211> LENGTH: 5
<212> TYPE: PRT
<213> ORGANISM: Artificial sequence
<220> FEATURE:
<223> OTHER INFORMATION: Amino acid sequence(Z)

<400> SEQUENCE: 12

Gly Ala Ala Gly Tyr
1               5

<210> SEQ ID NO 13
<211> LENGTH: 33
<212> TYPE: PRT
<213> ORGANISM: Artificial sequence
<220> FEATURE:
<223> OTHER INFORMATION: Amino acid sequence(T)

<400> SEQUENCE: 13

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 14
<211> LENGTH: 12
<212> TYPE: PRT
<213> ORGANISM: Artificial sequence
<220> FEATURE:
<223> OTHER INFORMATION: Polypeptide chain(S)

<400> SEQUENCE: 14

Gly Ala Gly Ala Gly Ser Gly Ala Gly Ala Gly Ser
1               5                   10

<210> SEQ ID NO 15
<211> LENGTH: 884
<212> TYPE: PRT
<213> ORGANISM: Artificial sequence
<220> FEATURE:
<223> OTHER INFORMATION: SELP8K

<400> SEQUENCE: 15

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
            35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80
```

```
Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
                115                 120                 125

Lys Gly Val Pro Gly Val Gly Val Pro Gly Val Gly Val Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
                180                 185                 190

Lys Gly Val Pro Gly Val Gly Val Pro Gly Val Gly Val Pro Gly Val
    195                 200                 205

Gly Val Pro Gly Ala Gly Ala Gly Ser Gly Ala Gly Ala Gly Ser Gly
            210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Lys Gly Val Pro Gly Val Gly Val Pro Gly Val Gly Val Pro Gly Val
            260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
                325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
            370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
                405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
                435                 440                 445

Lys Gly Val Pro Gly Val Gly Val Pro Gly Val Gly Val Pro Gly Val
    450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
            485                 490                 495
```

Gly Val Gly Val Pro Gly Val Gly Val Pro Gly Val Gly Val Pro Gly
            500                 505                 510
Lys Gly Val Pro Gly Val Gly Val Pro Gly Val Gly Val Pro Gly Val
        515                 520                 525
Gly Val Pro Gly Ala Gly Ala Gly Ser Gly Ala Gly Ala Gly Ser Gly
    530                 535                 540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
            565                 570                 575
Lys Gly Val Pro Gly Val Gly Val Pro Gly Val Gly Val Pro Gly Val
        580                 585                 590
Gly Val Pro Gly Ala Gly Ala Gly Ser Gly Ala Gly Ala Gly Ser Gly
    595                 600                 605
Ala Gly Ala Gly Ser Gly Ala Gly Ala Gly Ser Gly Val Gly Val Pro
    610                 615                 620
Gly Val Gly Val Pro Gly Val Gly Val Pro Gly Val Gly Val Pro Gly
625                 630                 635                 640
Lys Gly Val Pro Gly Val Gly Val Pro Gly Val Gly Val Pro Gly Val
            645                 650                 655
Gly Val Pro Gly Ala Gly Ala Gly Ser Gly Ala Gly Ala Gly Ser Gly
        660                 665                 670
Ala Gly Ala Gly Ser Gly Ala Gly Ala Gly Ser Gly Val Gly Val Pro
    675                 680                 685
Gly Val Gly Val Pro Gly Val Gly Val Pro Gly Val Gly Val Pro Gly
    690                 695                 700
Lys Gly Val Pro Gly Val Gly Val Pro Gly Val Gly Val Pro Gly Val
705                 710                 715                 720
Gly Val Pro Gly Ala Gly Ala Gly Ser Gly Ala Gly Ala Gly Ser Gly
            725                 730                 735
Ala Gly Ala Gly Ser Gly Ala Gly Ala Gly Ser Gly Val Gly Val Pro
        740                 745                 750
Gly Val Gly Val Pro Gly Val Gly Val Pro Gly Val Gly Val Pro Gly
    755                 760                 765
Lys Gly Val Pro Gly Val Gly Val Pro Gly Val Gly Val Pro Gly Val
    770                 775                 780
Gly Val Pro Gly Ala Gly Ala Gly Ser Gly Ala Gly Ala Gly Ser Gly
785                 790                 795                 800
Ala Gly Ala Gly Ser Gly Ala Gly Ala Gly Ser Gly Val Gly Val Pro
            805                 810                 815
Gly Val Gly Val Pro Gly Val Gly Val Pro Gly Val Gly Val Pro Gly
        820                 825                 830
Lys Gly Val Pro Gly Val Gly Val Pro Gly Val Gly Val Pro Gly Val
    835                 840                 845
Gly Val Pro Gly Ala Gly Ala Gly Ser Gly Ala Gly Ala Gly Ser Gly
    850                 855                 860
Ala Gly Ala Met Asp Pro Gly Arg Tyr Gln Asp Leu Arg Ser His His
865                 870                 875                 880
His His His His

<210> SEQ ID NO 16
<211> LENGTH: 948
<212> TYPE: PRT
<213> ORGANISM: Artificial sequence -continued

<220> FEATURE:
<223> OTHER INFORMATION: SELP0K

<400> SEQUENCE: 16

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
50                  55                  60

Pro Gly Lys Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
            85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
            115                 120                 125

Val Gly Val Pro Gly Val Gly Val Pro Gly Ala Gly Ala Gly Ser Gly
        130                 135                 140

Ala Gly Ala Gly Ser Gly Val Gly Val Pro Gly Val Gly Val Pro Gly
145                 150                 155                 160

Val Gly Val Pro Gly Val Gly Val Pro Gly Lys Gly Val Pro Gly Val
            165                 170                 175

Gly Val Pro Gly Val Gly Val Pro Gly Val Gly Val Pro Gly Ala Gly
            180                 185                 190

Ala Gly Ser Gly Ala Gly Ala Gly Ser Gly Val Gly Val Pro Gly Val
        195                 200                 205

Gly Val Pro Gly Val Gly Val Pro Gly Val Gly Val Pro Gly Lys Gly
        210                 215                 220

Val Pro Gly Val Gly Val Pro Gly Val Gly Val Pro Gly Val Gly Val
225                 230                 235                 240

Pro Gly Ala Gly Ala Gly Ser Gly Ala Gly Ala Gly Ser Gly Val Gly
            245                 250                 255

Val Pro Gly Val Gly Val Pro Gly Val Gly Val Pro Gly Val Gly Val
            260                 265                 270

Pro Gly Lys Gly Val Pro Gly Val Gly Val Pro Gly Val Gly Val Pro
        275                 280                 285

Gly Val Gly Val Pro Gly Ala Gly Ala Gly Ser Gly Ala Gly Ala Gly
        290                 295                 300

Ser Gly Val Gly Val Pro Gly Val Gly Val Pro Gly Val Gly Val Pro
305                 310                 315                 320

Gly Val Gly Val Pro Gly Lys Gly Val Pro Gly Val Gly Val Pro Gly
            325                 330                 335

Val Gly Val Pro Gly Val Gly Val Pro Gly Ala Gly Ala Gly Ser Gly
            340                 345                 350

Ala Gly Ala Gly Ser Gly Val Gly Val Pro Gly Val Gly Val Pro Gly
        355                 360                 365

Val Gly Val Pro Gly Val Gly Val Pro Gly Lys Gly Val Pro Gly Val
        370                 375                 380

Gly Val Pro Gly Val Gly Val Pro Gly Val Gly Val Pro Gly Ala Gly
385                 390                 395                 400

```
Ala Gly Ser Gly Ala Gly Ala Gly Ser Gly Val Gly Val Pro Gly Val
            405                 410                 415
Gly Val Pro Gly Val Gly Val Pro Gly Val Gly Val Pro Gly Lys Gly
            420                 425                 430
Val Pro Gly Val Gly Val Pro Gly Val Gly Val Pro Gly Val Gly Val
            435                 440                 445
Pro Gly Ala Gly Ala Gly Ser Gly Ala Gly Ala Gly Ser Gly Val Gly
            450                 455                 460
Val Pro Gly Val Gly Val Pro Gly Val Gly Val Pro Gly Val Gly Val
465                 470                 475                 480
Pro Gly Lys Gly Val Pro Gly Val Gly Val Pro Gly Val Gly Val Pro
            485                 490                 495
Gly Val Gly Val Pro Gly Ala Gly Ala Gly Ser Gly Ala Gly Ala Gly
            500                 505                 510
Ser Gly Val Gly Val Pro Gly Val Gly Val Pro Gly Val Gly Val Pro
            515                 520                 525
Gly Val Gly Val Pro Gly Lys Gly Val Pro Gly Val Gly Val Pro Gly
            530                 535                 540
Val Gly Val Pro Gly Val Gly Val Pro Gly Ala Gly Ala Gly Ser Gly
545                 550                 555                 560
Ala Gly Ala Gly Ser Gly Val Gly Val Pro Gly Val Gly Val Pro Gly
            565                 570                 575
Val Gly Val Pro Gly Val Gly Val Pro Gly Lys Gly Val Pro Gly Val
            580                 585                 590
Gly Val Pro Gly Val Gly Val Pro Gly Val Gly Val Pro Gly Ala Gly
            595                 600                 605
Ala Gly Ser Gly Ala Gly Ala Gly Ser Gly Val Gly Val Pro Gly Val
            610                 615                 620
Gly Val Pro Gly Val Gly Val Pro Gly Val Gly Val Pro Gly Lys Gly
625                 630                 635                 640
Val Pro Gly Val Gly Val Pro Gly Val Gly Val Pro Gly Val Gly Val
            645                 650                 655
Pro Gly Ala Gly Ala Gly Ser Gly Ala Gly Ala Gly Ser Gly Val Gly
            660                 665                 670
Val Pro Gly Val Gly Val Pro Gly Val Gly Val Pro Gly Val Gly Val
            675                 680                 685
Pro Gly Lys Gly Val Pro Gly Val Gly Val Pro Gly Val Gly Val Pro
            690                 695                 700
Gly Val Gly Val Pro Gly Ala Gly Ala Gly Ser Gly Ala Gly Ala Gly
705                 710                 715                 720
Ser Gly Val Gly Val Pro Gly Val Gly Val Pro Gly Val Gly Val Pro
            725                 730                 735
Gly Val Gly Val Pro Gly Lys Gly Val Pro Gly Val Gly Val Pro Gly
            740                 745                 750
Val Gly Val Pro Gly Val Gly Val Pro Gly Ala Gly Ala Gly Ser Gly
            755                 760                 765
Ala Gly Ala Gly Ser Gly Val Gly Val Pro Gly Val Gly Val Pro Gly
            770                 775                 780
Val Gly Val Pro Gly Val Gly Val Pro Gly Lys Gly Val Pro Gly Val
785                 790                 795                 800
Gly Val Pro Gly Val Gly Val Pro Gly Val Gly Val Pro Gly Ala Gly
            805                 810                 815
```

```
Ala Gly Ser Gly Ala Gly Ala Gly Ser Gly Val Val Pro Gly Val
            820                 825                 830

Gly Val Pro Gly Val Gly Val Pro Gly Val Gly Val Pro Gly Lys Gly
        835                 840                 845

Val Pro Gly Val Gly Val Pro Gly Val Gly Val Pro Gly Val Gly Val
    850                 855                 860

Pro Gly Ala Gly Ala Gly Ser Gly Ala Gly Ala Gly Ser Gly Val Gly
865                 870                 875                 880

Val Pro Gly Val Gly Val Pro Gly Val Gly Val Pro Gly Val Gly Val
            885                 890                 895

Pro Gly Lys Gly Val Pro Gly Val Gly Val Pro Gly Val Gly Val Pro
        900                 905                 910

Gly Val Gly Val Pro Gly Ala Gly Ala Gly Ser Gly Ala Gly Ala Gly
            915                 920                 925

Ser Gly Ala Met Asp Pro Gly Arg Tyr Gln Asp Leu Arg Ser His His
        930                 935                 940

His His His His
945

<210> SEQ ID NO 17
<211> LENGTH: 1384
<212> TYPE: PRT
<213> ORGANISM: Artificial sequence
<220> FEATURE:
<223> OTHER INFORMATION: SLP4.1

<400> SEQUENCE: 17

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Ala Gly
        35                  40                  45

Ala Gly Ser Gly Ala Gly Ala Gly Ser Gly Ala Gly Ala Gly Ser Gly
    50                  55                  60

Ala Gly Ala Gly Ser Gly Val Gly Val Pro Gly Val Gly Val Pro Gly
65                  70                  75                  80

Ala Gly Ala Gly Ser Gly Ala Gly Ala Gly Ser Gly Ala Gly Ala Gly
            85                  90                  95

Ser Gly Ala Gly Ala Gly Ser Gly Ala Gly Ala Gly Ser Gly Ala Gly
            100                 105                 110

Ala Gly Ser Gly Val Gly Val Pro Gly Val Gly Val Pro Gly Ala Gly
            115                 120                 125

Ala Gly Ser Gly Ala Gly Ala Gly Ser Gly Ala Gly Ala Gly Ser Gly
            130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Ala Gly Ala Gly
            165                 170                 175

Ser Gly Ala Gly Ala Gly Ser Gly Ala Gly Ala Gly Ser Gly Ala Gly
            180                 185                 190

Ala Gly Ser Gly Ala Gly Ala Gly Ser Gly Ala Gly Ala Gly Ser Gly
            195                 200                 205

Val Gly Val Pro Gly Val Gly Val Pro Gly Ala Gly Ala Gly Ser Gly
    210                 215                 220
```

-continued

```
Ala Gly Ala Gly Ser Gly Ala Gly Ala Gly Ser Gly Ala Gly
225                 230                 235                 240

Ser Gly Ala Gly Ala Gly Ser Gly Ala Gly Ala Gly Val Gly
                245                 250                 255

Val Pro Gly Val Gly Val Pro Gly Ala Gly Ala Gly Ser Gly Ala Gly
        260                 265                 270

Ala Gly Ser Gly Ala Gly Ala Gly Ser Gly Ala Gly Ala Gly Ser Gly
        275                 280                 285

Ala Gly Ala Gly Ser Gly Ala Gly Ala Gly Ser Gly Val Gly Val Pro
        290                 295                 300

Gly Val Gly Val Pro Gly Ala Gly Ala Gly Ser Gly Ala Gly Ala Gly
305                 310                 315                 320

Ser Gly Ala Gly Ala Gly Ser Gly Ala Gly Ala Gly Ser Gly Ala Gly
                325                 330                 335

Ala Gly Ser Gly Ala Gly Ala Gly Ser Gly Val Gly Val Pro Gly Val
                340                 345                 350

Gly Val Pro Gly Ala Gly Ala Gly Ser Gly Ala Gly Ala Gly Ser Gly
        355                 360                 365

Ala Gly Ala Gly Ser Gly Ala Gly Ala Gly Ser Gly Ala Gly Ala Gly
        370                 375                 380

Ser Gly Ala Gly Ala Gly Ser Gly Val Gly Val Pro Gly Val Gly Val
385                 390                 395                 400

Pro Gly Ala Gly Ala Gly Ser Gly Ala Gly Ala Gly Ser Gly Ala Gly
                405                 410                 415

Ala Gly Ser Gly Ala Gly Ala Gly Ser Gly Ala Gly Ala Gly Ser Gly
                420                 425                 430

Ala Gly Ala Gly Ser Gly Val Gly Val Pro Gly Val Gly Val Pro Gly
                435                 440                 445

Ala Gly Ala Gly Ser Gly Ala Gly Ala Gly Ser Gly Ala Gly Ala Gly
        450                 455                 460

Ser Gly Ala Gly Ala Gly Ser Gly Ala Gly Ala Gly Ser Gly Ala Gly
465                 470                 475                 480

Ala Gly Ser Gly Val Gly Val Pro Gly Val Gly Val Pro Gly Ala Gly
                485                 490                 495

Ala Gly Ser Gly Ala Gly Ala Gly Ser Gly Ala Gly Ala Gly Ser Gly
                500                 505                 510

Ala Gly Ala Gly Ser Gly Ala Gly Ala Gly Ser Gly Ala Gly Ala Gly
        515                 520                 525

Ser Gly Val Gly Val Pro Gly Val Gly Val Pro Gly Ala Gly Ala Gly
        530                 535                 540

Ser Gly Ala Gly Ala Gly Ser Gly Ala Gly Ala Gly Ser Gly Ala Gly
545                 550                 555                 560

Ala Gly Ser Gly Ala Gly Ala Gly Ser Gly Ala Gly Ala Gly Ser Gly
                565                 570                 575

Val Gly Val Pro Gly Val Gly Val Pro Gly Ala Gly Ala Gly Ser Gly
                580                 585                 590

Ala Gly Ala Gly Ser Gly Ala Gly Ala Gly Ser Gly Ala Gly Ala Gly
        595                 600                 605

Ser Gly Ala Gly Ala Gly Ser Gly Ala Gly Ala Gly Ser Gly Val Gly
        610                 615                 620

Val Pro Gly Val Gly Val Pro Gly Ala Gly Ala Gly Ser Gly Ala Gly
625                 630                 635                 640
```

```
Ala Gly Ser Gly Ala Gly Ala Gly Ser Gly Ala Gly Ser Gly
            645                 650                 655
Ala Gly Ala Gly Ser Gly Ala Gly Ala Gly Ser Gly Val Gly Val Pro
            660                 665                 670
Gly Val Gly Val Pro Gly Ala Gly Ala Gly Ser Gly Ala Gly Ala Gly
            675                 680                 685
Ser Gly Ala Gly Ala Gly Ser Gly Ala Gly Ala Gly Ser Gly Ala Gly
            690                 695                 700
Ala Gly Ser Gly Ala Gly Ala Gly Ser Gly Val Gly Val Pro Gly Val
705                 710                 715                 720
Gly Val Pro Gly Ala Gly Ala Gly Ser Gly Ala Gly Ala Gly Ser Gly
            725                 730                 735
Ala Gly Ala Gly Ser Gly Ala Gly Ala Gly Ser Gly Ala Gly Ala Gly
            740                 745                 750
Ser Gly Ala Gly Ala Gly Ser Gly Val Gly Val Pro Gly Val Gly Val
            755                 760                 765
Pro Gly Ala Gly Ala Gly Ser Gly Ala Gly Ala Gly Ser Gly Ala Gly
            770                 775                 780
Ala Gly Ser Gly Ala Gly Ala Gly Ser Gly Ala Gly Ala Gly Ser Gly
785                 790                 795                 800
Ala Gly Ala Gly Ser Gly Val Gly Val Pro Gly Val Gly Val Pro Gly
            805                 810                 815
Ala Gly Ala Gly Ser Gly Ala Gly Ala Gly Ser Gly Ala Gly Ala Gly
            820                 825                 830
Ser Gly Ala Gly Ala Gly Ser Gly Ala Gly Ala Gly Ser Gly Ala Gly
            835                 840                 845
Ala Gly Ser Gly Val Gly Val Pro Gly Val Gly Val Pro Gly Ala Gly
            850                 855                 860
Ala Gly Ser Gly Ala Gly Ala Gly Ser Gly Ala Gly Ala Gly Ser Gly
865                 870                 875                 880
Ala Gly Ala Gly Ser Gly Ala Gly Ala Gly Ser Gly Ala Gly Ala Gly
            885                 890                 895
Ser Gly Val Gly Val Pro Gly Val Gly Val Pro Gly Ala Gly Ala Gly
            900                 905                 910
Ser Gly Ala Gly Ala Gly Ser Gly Ala Gly Ala Gly Ser Gly Ala Gly
            915                 920                 925
Ala Gly Ser Gly Ala Gly Ala Gly Ser Gly Ala Gly Ala Gly Ser Gly
            930                 935                 940
Val Gly Val Pro Gly Val Gly Val Pro Gly Ala Gly Ala Gly Ser Gly
945                 950                 955                 960
Ala Gly Ala Gly Ser Gly Ala Gly Ala Gly Ser Gly Ala Gly Ala Gly
            965                 970                 975
Ser Gly Ala Gly Ala Gly Ser Gly Ala Gly Ala Gly Ser Gly Val Gly
            980                 985                 990
Val Pro Gly Val Gly Val Pro Gly Ala Gly Ala Gly Ser Gly Ala Gly
            995                 1000                1005
Ala Gly Ser Gly Ala Gly Ala Gly Ser Gly Ala Gly Ala Gly Ser
            1010                1015                1020
Gly Ala Gly Ala Gly Ser Gly Ala Gly Ala Gly Ser Gly Val Gly
            1025                1030                1035
Val Pro Gly Val Gly Val Pro Gly Ala Gly Ala Gly Ser Gly Ala
            1040                1045                1050
```

```
Gly Ala  Gly Ser Gly Ala  Gly Ala Gly Ser  Gly Ala Gly
    1055             1060              1065

Ser Gly  Ala Gly Ala Gly  Ser Gly Ala Gly   Ser Gly Val
    1070             1075              1080

Gly Val  Pro Gly Val Gly  Val Pro Gly Ala   Gly Ser Gly
    1085             1090              1095

Ala Gly  Ala Gly Ser Gly  Ala Gly Ser Gly   Ala Gly Ala
    1100             1105              1110

Gly Ser  Gly Ala Gly Ala  Gly Ser Gly Ala   Gly Ser Gly
    1115             1120              1125

Val Gly  Val Pro Gly Val  Gly Val Pro Gly   Ala Gly Ser
    1130             1135              1140

Gly Ala  Gly Ala Gly Ser  Gly Ala Gly Ser   Gly Ala Gly
    1145             1150              1155

Ala Gly  Ser Gly Ala Gly  Ala Gly Ser Gly   Ala Gly Ser
    1160             1165              1170

Gly Val  Gly Val Pro Gly  Val Gly Val Pro   Gly Ala Gly
    1175             1180              1185

Ser Gly  Ala Gly Ala Gly  Ser Gly Ala Gly   Ser Gly Ala
    1190             1195              1200

Gly Ala  Gly Ser Gly Ala  Gly Ser Gly Ala   Gly Ala Gly
    1205             1210              1215

Ser Gly  Val Gly Val Pro  Gly Val Gly Val   Pro Gly Ala
    1220             1225              1230

Gly Ser  Gly Ala Gly Ala  Gly Ser Gly Ala   Gly Ser Gly
    1235             1240              1245

Ala Gly  Ala Gly Ser Gly  Ala Gly Ser Gly   Ala Gly Ala
    1250             1255              1260

Gly Ser  Gly Val Gly Val  Pro Gly Val Gly   Val Pro Gly
    1265             1270              1275

Ala Gly  Ser Gly Ala Gly  Ala Gly Ser Gly   Ala Gly Ser
    1280             1285              1290

Gly Ala  Gly Ala Gly Ser  Gly Ala Gly Ser   Gly Ala Gly
    1295             1300              1305

Ala Gly  Ser Gly Val Gly  Val Pro Gly Val   Gly Val Pro
    1310             1315              1320

Gly Ala  Gly Ser Gly Ala  Gly Ala Gly Ser   Gly Ala Gly
    1325             1330              1335

Ser Gly  Ala Gly Ala Gly  Ser Gly Ala Gly   Ser Gly Ala
    1340             1345              1350

Gly Ala  Gly Ser Gly Val  Gly Val Pro Gly   Val Pro Met
    1355             1360              1365

Asp Pro  Gly Arg Tyr Gln  Asp Leu Arg Ser   His His His
    1370             1375              1380

His

<210> SEQ ID NO 18
<211> LENGTH: 2690
<212> TYPE: PRT
<213> ORGANISM: Artificial Sequence
<220> FEATURE:
<223> OTHER INFORMATION: ELP 1.1
```

<400> SEQUENCE: 18

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Val Pro Gly Val Gly Val Pro Gly Val Gly Val Pro Gly Val Gly
            35                  40                  45

Val Pro Gly Val Gly Val Gly Ala Gly Ala Gly Ser Val Pro Gly Val Gly
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro Gly
            100                 105                 110

Val Gly Val Pro Gly Val Gly Ala Gly Ala Gly Ser Val Pro Gly
            115                 120                 125

Gly Val Gly Val Pro Gly Val Gly Val Pro Gly Val Gly Val Pro Gly Val
            130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Gly Ala Gly Ala Gly Ser Val
                180                 185                 190

Pro Gly Val Gly Val Pro Gly Val Gly Val Pro Gly Val Gly Val Pro
                195                 200                 205

Gly Val Gly Val Pro Gly Val Gly Val Pro Gly Val Gly Val Pro Gly
            210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Gly Ala Gly Ala Gly
                245                 250                 255

Ser Val Pro Gly Val Gly Val Pro Gly Val Gly Val Pro Gly Val Gly
                260                 265                 270

Val Pro Gly Val Gly Val Pro Gly Val Gly Val Pro Gly Val Gly Val
            275                 280                 285

Pro Gly Val Gly Val Pro Gly Val Gly Val Pro Gly Val Gly Val Pro
290                 295                 300

Gly Val Gly Val Pro Gly Val Gly Val Pro Gly Val Gly Gly Ala Gly
305                 310                 315                 320

Ala Gly Ser Val Pro Gly Val Gly Val Pro Gly Val Gly Val Pro Gly
                325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
            355                 360                 365

Val Pro Gly Val Gly Val Pro Gly Val Gly Val Pro Gly Val Gly Gly
            370                 375                 380

Ala Gly Ala Gly Ser Val Pro Gly Val Gly Val Pro Gly Val Gly Val
385                 390                 395                 400
```

-continued

Pro Gly Val Gly Val Pro Gly Val Gly Val Pro
            405                 410             415

Gly Val Gly Val Pro Gly Val Gly Val Pro Gly
            420                 425             430

Val Gly Val Pro Gly Val Gly Val Pro Gly Val
            435                 440             445

Gly Gly Ala Gly Ala Gly Ser Val Pro Gly Val Gly Val
450                 455                 460

Gly Val Pro Gly Val Gly Val Pro Gly Val Gly Val Gly
465             470                 475             480

Val Pro Gly Val Gly Val Pro Gly Val Gly Val Gly Val
            485                 490             495

Pro Gly Val Gly Val Pro Gly Val Gly Val Pro
            500                 505             510

Gly Val Gly Gly Ala Gly Ala Gly Ser Val Pro Gly Val Gly Val Pro
            515                 520             525

Gly Val Gly Val Pro Gly Val Gly Val Pro Gly
            530                 535             540

Val Gly Val Pro Gly Val Gly Val Pro Gly Val
545             550                 555             560

Gly Val Pro Gly Val Gly Val Pro Gly Val Gly
            565                 570             575

Val Pro Gly Val Gly Gly Ala Gly Ala Gly Ser Val Pro Gly Val Gly
            580                 585             590

Val Pro Gly Val Gly Val Pro Gly Val Gly Val
            595                 600             605

Pro Gly Val Gly Val Pro Gly Val Gly Val Pro
610                 615             620

Gly Val Gly Val Pro Gly Val Gly Val Pro Gly
625             630                 635             640

Val Gly Val Pro Gly Val Gly Gly Ala Gly Ala Gly Ser Val Pro Gly
            645                 650             655

Val Gly Val Pro Gly Val Gly Val Pro Gly Val
            660                 665             670

Gly Val Pro Gly Val Gly Val Pro Gly Val Gly
            675                 680             685

Val Pro Gly Val Gly Val Pro Gly Val Gly Val
            690                 695             700

Pro Gly Val Gly Val Pro Gly Val Gly Gly Ala Gly Ala Gly Ser Val
705                 710             715             720

Pro Gly Val Gly Val Pro Gly Val Gly Val Pro
            725                 730             735

Gly Val Gly Val Pro Gly Val Gly Val Pro Gly
            740                 745             750

Val Gly Val Pro Gly Val Gly Val Pro Gly Val
            755                 760             765

Gly Val Pro Gly Val Gly Val Pro Gly Val Gly Val Gly
            770                 775             780

Ser Val Pro Gly Val Gly Val Pro Gly Val Gly
785             790                 795             800

Val Pro Gly Val Gly Val Pro Gly Val Gly Val
            805                 810             815

-continued

Pro Gly Val Gly Val Pro Gly Val Gly Val Pro
              820                 825                 830

Gly Val Gly Val Pro Gly Val Gly Val Pro Gly Val Gly Ala Gly
              835                 840                 845

Ala Gly Ser Val Pro Gly Val Gly Val Pro Gly Val Gly Val Pro Gly
              850                 855                 860

Val Gly Val Pro Gly Val Gly Val Pro Gly Val Gly Val Pro Gly Val
865                 870                 875                 880

Gly Val Pro Gly Val Gly Val Pro Gly Val Gly Val Pro Gly Val Gly
                    885                 890                 895

Val Pro Gly Val Gly Val Pro Gly Val Gly Val Pro Gly Val Gly Gly
              900                 905                 910

Ala Gly Ala Gly Ser Val Pro Gly Val Gly Val Pro Gly Val Gly Val
              915                 920                 925

Pro Gly Val Gly Val Pro Gly Val Gly Val Pro Gly Val Gly Val Pro
              930                 935                 940

Gly Val Gly Val Pro Gly Val Gly Val Pro Gly Val Gly Val Pro Gly
945                 950                 955                 960

Val Gly Val Pro Gly Val Gly Val Pro Gly Val Gly Val Pro Gly Val
              965                 970                 975

Gly Gly Ala Gly Ala Gly Ser Val Pro Gly Val Gly Val Pro Gly Val
              980                 985                 990

Gly Val Pro Gly Val Gly Val Pro  Gly Val Gly Val Pro  Gly Val Gly
              995                 1000                1005

Val Pro Gly Val Gly Val Pro  Gly Val Gly Val Pro  Gly Val Gly
              1010                1015                1020

Val Pro Gly Val Gly Val Pro  Gly Val Gly Val Pro  Gly Val Gly
              1025                1030                1035

Val Pro Gly Val Gly Gly Ala  Gly Ala Gly Ser Val  Pro Gly Val
              1040                1045                1050

Gly Val Pro Gly Val Gly Val  Pro Gly Val Gly Val  Pro Gly Val
              1055                1060                1065

Gly Val Pro Gly Val Gly Val  Pro Gly Val Gly Val  Pro Gly Val
              1070                1075                1080

Gly Val Pro Gly Val Gly Val  Pro Gly Val Gly Val  Pro Gly Val
              1085                1090                1095

Gly Val Pro Gly Val Gly Val  Pro Gly Val Gly Gly  Ala Gly Ala
              1100                1105                1110

Gly Ser Val Pro Gly Val Gly  Val Pro Gly Val Gly  Val Pro Gly
              1115                1120                1125

Val Gly Val Pro Gly Val Gly  Val Pro Gly Val Gly  Val Pro Gly
              1130                1135                1140

Val Gly Val Pro Gly Val Gly  Val Pro Gly Val Gly  Val Pro Gly
              1145                1150                1155

Val Gly Val Pro Gly Val Gly  Val Pro Gly Val Gly  Val Pro Gly
              1160                1165                1170

Val Gly Gly Ala Gly Ala Gly  Ser Val Pro Gly Val  Gly Val Pro
              1175                1180                1185

Gly Val Gly Val Pro Gly Val  Gly Val Pro Gly Val  Gly Val Pro
              1190                1195                1200

Gly Val Gly Val Pro Gly Val  Gly Val Pro Gly Val  Gly Val Pro
              1205                1210                1215

```
Gly Val Gly Val Pro Gly Val Gly Val Pro Gly Val Pro
    1220            1225            1230

Gly Val Gly Val Pro Gly Val Gly Ala Gly Ala Gly Ser Val
    1235            1240            1245

Pro Gly Val Gly Val Pro Val Gly Val Pro Gly Val Gly Val
    1250            1255            1260

Pro Gly Val Gly Val Pro Val Gly Val Pro Gly Val Gly Val
    1265            1270            1275

Pro Gly Val Gly Val Pro Val Gly Val Pro Gly Val Gly Val
    1280            1285            1290

Pro Gly Val Gly Val Pro Val Gly Val Pro Gly Val Gly Gly
    1295            1300            1305

Ala Gly Ala Gly Ser Val Pro Gly Val Gly Val Pro Gly Val Gly
    1310            1315            1320

Val Pro Gly Val Gly Val Pro Gly Val Gly Val Pro Gly Val Gly
    1325            1330            1335

Val Pro Gly Val Gly Val Pro Gly Val Gly Val Pro Gly Val Gly
    1340            1345            1350

Val Pro Gly Val Gly Val Pro Gly Val Gly Val Pro Gly Val Gly
    1355            1360            1365

Val Pro Gly Val Gly Gly Ala Gly Ala Gly Ser Val Pro Gly Val
    1370            1375            1380

Gly Val Pro Gly Val Gly Val Pro Gly Val Gly Val Pro Gly Val
    1385            1390            1395

Gly Val Pro Gly Val Gly Val Pro Gly Val Gly Val Pro Gly Val
    1400            1405            1410

Gly Val Pro Gly Val Gly Val Pro Gly Val Gly Val Pro Gly Val
    1415            1420            1425

Gly Val Pro Gly Val Gly Val Pro Gly Val Gly Gly Ala Gly Ala
    1430            1435            1440

Gly Ser Val Pro Gly Val Gly Val Pro Gly Val Gly Val Pro Gly
    1445            1450            1455

Val Gly Val Pro Gly Val Gly Val Pro Gly Val Gly Val Pro Gly
    1460            1465            1470

Val Gly Val Pro Gly Val Gly Val Pro Gly Val Gly Val Pro Gly
    1475            1480            1485

Val Gly Val Pro Gly Val Gly Val Pro Gly Val Gly Val Pro Gly
    1490            1495            1500

Val Gly Gly Ala Gly Ala Gly Ser Val Pro Gly Val Gly Val Pro
    1505            1510            1515

Gly Val Gly Val Pro Gly Val Gly Val Pro Gly Val Gly Val Pro
    1520            1525            1530

Gly Val Gly Val Pro Gly Val Gly Val Pro Gly Val Gly Val Pro
    1535            1540            1545

Gly Val Gly Val Pro Gly Val Gly Val Pro Gly Val Gly Val Pro
    1550            1555            1560

Gly Val Gly Val Pro Gly Val Gly Gly Ala Gly Ala Gly Ser Val
    1565            1570            1575

Pro Gly Val Gly Val Pro Gly Val Gly Val Pro Gly Val Gly Val
    1580            1585            1590

Pro Gly Val Gly Val Pro Gly Val Gly Val Pro Gly Val Gly Val
    1595            1600            1605
```

```
Pro Gly  Val Gly Val Pro  Gly Val Gly Val Pro  Gly Val Gly Val
    1610              1615              1620

Pro Gly  Val Gly Val Pro  Gly Val Gly Val Pro  Gly Val Gly Gly
    1625              1630              1635

Ala Gly  Ala Gly Ser Val  Pro Gly Val Gly Val  Pro Gly Val Gly
    1640              1645              1650

Val Pro  Gly Val Gly Val  Pro Gly Val Gly Val  Pro Gly Val Gly
    1655              1660              1665

Val Pro  Gly Val Gly Val  Pro Gly Val Gly Val  Pro Gly Val Gly
    1670              1675              1680

Val Pro  Gly Val Gly Val  Pro Gly Val Gly Val  Pro Gly Val Gly
    1685              1690              1695

Val Pro  Gly Val Gly Gly  Ala Gly Ala Gly Ser  Val Pro Gly Val
    1700              1705              1710

Gly Val  Pro Gly Val Gly  Val Pro Gly Val Gly  Val Pro Gly Val
    1715              1720              1725

Gly Val  Pro Gly Val Gly  Val Pro Gly Val Gly  Val Pro Gly Val
    1730              1735              1740

Gly Val  Pro Gly Val Gly  Val Pro Gly Val Gly  Val Pro Gly Val
    1745              1750              1755

Gly Val  Pro Gly Val Gly  Val Pro Gly Val Gly  Gly Ala Gly Ala
    1760              1765              1770

Gly Ser  Val Pro Gly Val  Gly Val Pro Gly Val  Gly Val Pro Gly
    1775              1780              1785

Val Gly  Val Pro Gly Val  Gly Val Pro Gly Val  Gly Val Pro Gly
    1790              1795              1800

Val Gly  Val Pro Gly Val  Gly Val Pro Gly Val  Gly Val Pro Gly
    1805              1810              1815

Val Gly  Val Pro Gly Val  Gly Val Pro Gly Val  Gly Val Pro Gly
    1820              1825              1830

Val Gly  Gly Ala Gly Ala  Gly Ser Val Pro Gly  Val Gly Val Pro
    1835              1840              1845

Gly Val  Gly Val Pro Gly  Val Gly Val Pro Gly  Val Gly Val Pro
    1850              1855              1860

Gly Val  Gly Val Pro Gly  Val Gly Val Pro Gly  Val Gly Val Pro
    1865              1870              1875

Gly Val  Gly Val Pro Gly  Val Gly Val Pro Gly  Val Gly Val Pro
    1880              1885              1890

Gly Val  Gly Val Pro Gly  Val Gly Gly Ala Gly  Ala Gly Ser Val
    1895              1900              1905

Pro Gly  Val Gly Val Pro  Gly Val Gly Val Pro  Gly Val Gly Val
    1910              1915              1920

Pro Gly  Val Gly Val Pro  Gly Val Gly Val Pro  Gly Val Gly Val
    1925              1930              1935

Pro Gly  Val Gly Val Pro  Gly Val Gly Val Pro  Gly Val Gly Val
    1940              1945              1950

Pro Gly  Val Gly Val Pro  Gly Val Gly Val Pro  Gly Val Gly Gly
    1955              1960              1965

Ala Gly  Ala Gly Ser Val  Pro Gly Val Gly Val  Pro Gly Val Gly
    1970              1975              1980

Val Pro  Gly Val Gly Val  Pro Gly Val Gly Val  Pro Gly Val Gly
    1985              1990              1995
```

```
Val Pro Gly Val Gly Val Pro Gly Val Gly Val Pro Gly Val Gly
2000                2005                2010
Val Pro Gly Val Gly Val Pro Gly Val Gly Val Pro Gly Val Gly
2015                2020                2025
Val Pro Gly Val Gly Gly Ala Gly Ala Gly Ser Val Pro Gly Val
2030                2035                2040
Gly Val Pro Gly Val Gly Val Pro Gly Val Gly Val Pro Gly Val
2045                2050                2055
Gly Val Pro Gly Val Gly Val Pro Gly Val Gly Val Pro Gly Val
2060                2065                2070
Gly Val Pro Gly Val Gly Val Pro Gly Val Gly Val Pro Gly Val
2075                2080                2085
Gly Val Pro Gly Val Gly Val Pro Gly Val Gly Gly Ala Gly Ala
2090                2095                2100
Gly Ser Val Pro Gly Val Gly Val Pro Gly Val Gly Val Pro Gly
2105                2110                2115
Val Gly Val Pro Gly Val Gly Val Pro Gly Val Gly Val Pro Gly
2120                2125                2130
Val Gly Val Pro Gly Val Gly Val Pro Gly Val Gly Val Pro Gly
2135                2140                2145
Val Gly Val Pro Gly Val Gly Val Pro Gly Val Gly Val Pro Gly
2150                2155                2160
Val Gly Gly Ala Gly Ala Gly Ser Val Pro Gly Val Gly Val Pro
2165                2170                2175
Gly Val Gly Val Pro Gly Val Gly Val Pro Gly Val Gly Val Pro
2180                2185                2190
Gly Val Gly Val Pro Gly Val Gly Val Pro Gly Val Gly Val Pro
2195                2200                2205
Gly Val Gly Val Pro Gly Val Gly Val Pro Gly Val Gly Val Pro
2210                2215                2220
Gly Val Gly Val Pro Gly Val Gly Gly Ala Gly Ala Gly Ser Val
2225                2230                2235
Pro Gly Val Gly Val Pro Gly Val Gly Val Pro Gly Val Gly Val
2240                2245                2250
Pro Gly Val Gly Val Pro Gly Val Gly Val Pro Gly Val Gly Val
2255                2260                2265
Pro Gly Val Gly Val Pro Gly Val Gly Val Pro Gly Val Gly Val
2270                2275                2280
Pro Gly Val Gly Val Pro Gly Val Gly Val Pro Gly Val Gly Gly
2285                2290                2295
Ala Gly Ala Gly Ser Val Pro Gly Val Gly Val Pro Gly Val Gly
2300                2305                2310
Val Pro Gly Val Gly Val Pro Gly Val Gly Val Pro Gly Val Gly
2315                2320                2325
Val Pro Gly Val Gly Val Pro Gly Val Gly Val Pro Gly Val Gly
2330                2335                2340
Val Pro Gly Val Gly Val Pro Gly Val Gly Val Pro Gly Val Gly
2345                2350                2355
Val Pro Gly Val Gly Gly Ala Gly Ala Gly Ser Val Pro Gly Val
2360                2365                2370
Gly Val Pro Gly Val Gly Val Pro Gly Val Gly Val Pro Gly Val
2375                2380                2385
```

-continued

```
Gly Val Pro Gly Val Gly Val Pro Gly Val Gly Val Pro Gly Val
        2390                2395                2400

Gly Val Pro Gly Val Gly Val Pro Gly Val Gly Val Pro Gly Val
        2405                2410                2415

Gly Val Pro Gly Val Gly Val Pro Gly Val Gly Gly Ala Gly Ala
        2420                2425                2430

Gly Ser Val Pro Gly Val Gly Val Pro Gly Val Gly Val Pro Gly
        2435                2440                2445

Val Gly Val Pro Gly Val Gly Val Pro Gly Val Gly Val Pro Gly
        2450                2455                2460

Val Gly Val Pro Gly Val Gly Val Pro Gly Val Gly Val Pro Gly
        2465                2470                2475

Val Gly Val Pro Gly Val Gly Val Pro Gly Val Gly Val Pro Gly
        2480                2485                2490

Val Gly Gly Ala Gly Ala Gly Ser Val Pro Gly Val Gly Val Pro
        2495                2500                2505

Gly Val Gly Val Pro Gly Val Gly Val Pro Gly Val Gly Val Pro
        2510                2515                2520

Gly Val Gly Val Pro Gly Val Gly Val Pro Gly Val Gly Val Pro
        2525                2530                2535

Gly Val Gly Val Pro Gly Val Gly Val Pro Gly Val Gly Val Pro
        2540                2545                2550

Gly Val Gly Val Pro Gly Val Gly Gly Ala Gly Ala Gly Ser Val
        2555                2560                2565

Pro Gly Val Gly Val Pro Gly Val Gly Val Pro Gly Val Gly Val
        2570                2575                2580

Pro Gly Val Gly Val Pro Gly Val Gly Val Pro Gly Val Gly Val
        2585                2590                2595

Pro Gly Val Gly Val Pro Gly Val Gly Val Pro Gly Val Gly Val
        2600                2605                2610

Pro Gly Val Gly Val Pro Gly Val Gly Val Pro Gly Val Gly Gly
        2615                2620                2625

Ala Gly Ala Gly Ser Val Pro Gly Val Gly Val Pro Gly Val Gly
        2630                2635                2640

Val Pro Gly Val Gly Val Pro Gly Val Gly Val Pro Gly Val Gly
        2645                2650                2655

Val Pro Gly Val Gly Val Pro Gly Val Gly Val Pro Gly Val Gly
        2660                2665                2670

Met Asp Pro Gly Arg Tyr Gln Asp Leu Arg Ser His His His
        2675                2680                2685

His His
    2690

<210> SEQ ID NO 19
<211> LENGTH: 1534
<212> TYPE: PRT
<213> ORGANISM: Artificial Sequence
<220> FEATURE:
<223> OTHER INFORMATION: SLP4.1.3

<400> SEQUENCE: 19

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30
```

-continued

```
Met Gly Ala Gly Ser Gly Ala Gly Ala Gly Ser Gly Ala Gly
            35                  40                  45
Ser Gly Ala Gly Ala Gly Ser Gly Ala Gly Ala Gly Ser Gly Ala Gly
50                  55                  60
Ala Gly Ser Gly Ala Gly Ala Gly Ser Gly Ala Gly Ala Gly Ser Gly
65                  70                  75                  80
Ala Gly Ala Gly Ser Gly Ala Gly Ala Gly Ser Gly Ala Gly Ala Gly
            85                  90                  95
Ser Gly Ala Gly Ala Gly Ser Gly Lys Gly Val Pro Gly Lys Gly Val
            100                 105                 110
Pro Gly Ala Gly Ala Gly Ser Gly Ala Gly Ala Gly Ser Gly Ala Gly
            115                 120                 125
Ala Gly Ser Gly Ala Gly Ala Gly Ser Gly Ala Gly Ala Gly Ser Gly
            130                 135                 140
Ala Gly Ala Gly Ser Gly Ala Gly Ala Gly Ser Gly Ala Gly Ala Gly
145                 150                 155                 160
Ser Gly Ala Gly Ala Gly Ser Gly Ala Gly Ala Gly Ser Gly Lys Gly
                165                 170                 175
Val Pro Gly Lys Gly Val Pro Gly Ala Gly Ala Gly Ser Gly Ala Gly
            180                 185                 190
Ala Gly Ser Gly Ala Gly Ala Gly Ser Gly Ala Gly Ala Gly Ser Gly
            195                 200                 205
Ala Gly Ala Gly Ser Gly Ala Gly Ala Gly Ser Gly Ala Gly Ala Gly
            210                 215                 220
Ser Gly Ala Gly Ala Gly Ser Gly Ala Gly Ala Gly Ser Gly Ala Gly
225                 230                 235                 240
Ala Gly Ser Gly Lys Gly Val Pro Gly Lys Gly Val Pro Gly Ala Gly
            245                 250                 255
Ala Gly Ser Gly Ala Gly Ala Gly Ser Gly Ala Gly Ala Gly Ser Gly
            260                 265                 270
Ala Gly Ala Gly Ser Gly Ala Gly Ala Gly Ser Gly Ala Gly Ala Gly
            275                 280                 285
Ser Gly Ala Gly Ala Gly Ser Gly Ala Gly Ala Gly Ser Gly Ala Gly
            290                 295                 300
Ala Gly Ser Gly Ala Gly Ala Gly Ser Gly Lys Gly Val Pro Gly Lys
305                 310                 315                 320
Gly Val Pro Gly Ala Gly Ala Gly Ser Gly Ala Gly Ala Gly Ser Gly
            325                 330                 335
Ala Gly Ala Gly Ser Gly Ala Gly Ala Gly Ser Gly Ala Gly Ala Gly
            340                 345                 350
Ser Gly Ala Gly Ala Gly Ser Gly Ala Gly Ala Gly Ser Gly Ala Gly
            355                 360                 365
Ala Gly Ser Gly Ala Gly Ala Gly Ser Gly Ala Gly Ala Gly Ser Gly
            370                 375                 380
Lys Gly Val Pro Gly Lys Gly Val Pro Gly Ala Gly Ala Gly Ser Gly
385                 390                 395                 400
Ala Gly Ala Gly Ser Gly Ala Gly Ala Gly Ser Gly Ala Gly Ala Gly
            405                 410                 415
Ser Gly Ala Gly Ala Gly Ser Gly Ala Gly Ala Gly Ser Gly Ala Gly
            420                 425                 430
Ala Gly Ser Gly Ala Gly Ala Gly Ser Gly Ala Gly Ala Gly Ser Gly
            435                 440                 445
```

```
Ala Gly Ala Gly Ser Gly Lys Gly Val Pro Gly Lys Gly Val Pro Gly
        450                 455                 460
Ala Gly Ala Gly Ser Gly Ala Gly Ala Gly Ser Gly Ala Gly Ala Gly
465                 470                 475                 480
Ser Gly Ala Gly Ala Gly Ser Gly Ala Gly Ala Gly Ser Gly Ala Gly
                485                 490                 495
Ala Gly Ser Gly Ala Gly Ala Gly Ser Gly Ala Gly Ala Gly Ser Gly
        500                 505                 510
Ala Gly Ala Gly Ser Gly Ala Gly Ala Gly Ser Gly Lys Gly Val Pro
        515                 520                 525
Gly Lys Gly Val Pro Gly Ala Gly Ala Gly Ser Gly Ala Gly Ala Gly
        530                 535                 540
Ser Gly Ala Gly Ala Gly Ser Gly Ala Gly Ala Gly Ser Gly Ala Gly
545                 550                 555                 560
Ala Gly Ser Gly Ala Gly Ala Gly Ser Gly Ala Gly Ala Gly Ser Gly
                565                 570                 575
Ala Gly Ala Gly Ser Gly Ala Gly Ala Gly Ser Gly Ala Gly Ala Gly
        580                 585                 590
Ser Gly Lys Gly Val Pro Gly Lys Gly Val Pro Gly Ala Gly Ala Gly
        595                 600                 605
Ser Gly Ala Gly Ala Gly Ser Gly Ala Gly Ala Gly Ser Gly Ala Gly
        610                 615                 620
Ala Gly Ser Gly Ala Gly Ala Gly Ser Gly Ala Gly Ala Gly Ser Gly
625                 630                 635                 640
Ala Gly Ala Gly Ser Gly Ala Gly Ala Gly Ser Gly Ala Gly Ala Gly
                645                 650                 655
Ser Gly Ala Gly Ala Gly Ser Gly Lys Gly Val Pro Gly Lys Gly Val
        660                 665                 670
Pro Gly Ala Gly Ala Gly Ser Gly Ala Gly Ala Gly Ser Gly Ala Gly
        675                 680                 685
Ala Gly Ser Gly Ala Gly Ala Gly Ser Gly Ala Gly Ala Gly Ser Gly
        690                 695                 700
Ala Gly Ala Gly Ser Gly Ala Gly Ala Gly Ser Gly Ala Gly Ala Gly
705                 710                 715                 720
Ser Gly Ala Gly Ala Gly Ser Gly Ala Gly Ala Gly Ser Gly Lys Gly
                725                 730                 735
Val Pro Gly Lys Gly Val Pro Gly Ala Gly Ala Gly Ser Gly Ala Gly
        740                 745                 750
Ala Gly Ser Gly Ala Gly Ala Gly Ser Gly Ala Gly Ala Gly Ser Gly
        755                 760                 765
Ala Gly Ala Gly Ser Gly Ala Gly Ala Gly Ser Gly Ala Gly Ala Gly
        770                 775                 780
Ser Gly Ala Gly Ala Gly Ser Gly Ala Gly Ala Gly Ser Gly Ala Gly
785                 790                 795                 800
Ala Gly Ser Gly Lys Gly Val Pro Gly Lys Gly Val Pro Gly Ala Gly
                805                 810                 815
Ala Gly Ser Gly Ala Gly Ala Gly Ser Gly Ala Gly Ala Gly Ser Gly
        820                 825                 830
Ala Gly Ala Gly Ser Gly Ala Gly Ala Gly Ser Gly Ala Gly Ala Gly
        835                 840                 845
Ser Gly Ala Gly Ala Gly Ser Gly Ala Gly Ala Gly Ser Gly Ala Gly
        850                 855                 860
```

-continued

Ala Gly Ser Gly Ala Gly Ala Gly Ser Gly Lys Gly Val Pro Gly Lys
865                 870                 875                 880

Gly Val Pro Gly Ala Gly Ala Gly Ser Gly Ala Gly Ala Gly Ser Gly
            885                 890                 895

Ala Gly Ala Gly Ser Gly Ala Gly Ala Gly Ser Gly Ala Gly Ala Gly
        900                 905                 910

Ser Gly Ala Gly Ala Gly Ser Gly Ala Gly Ala Gly Ser Gly Ala Gly
    915                 920                 925

Ala Gly Ser Gly Ala Gly Ala Gly Ser Gly Ala Gly Ala Gly Ser Gly
930                 935                 940

Lys Gly Val Pro Gly Lys Gly Val Pro Gly Ala Gly Ala Gly Ser Gly
945                 950                 955                 960

Ala Gly Ala Gly Ser Gly Ala Gly Ala Gly Ser Gly Ala Gly Ala Gly
        965                 970                 975

Ser Gly Ala Gly Ala Gly Ser Gly Ala Gly Ala Gly Ser Gly Ala Gly
    980                 985                 990

Ala Gly Ser Gly Ala Gly Ala Gly Ser Gly Ala Gly Ala Gly Ser Gly
        995                 1000                1005

Ala Gly Ala Gly Ser Gly Lys Gly Val Pro Gly Lys Gly Val Pro
    1010            1015                1020

Gly Ala Gly Ala Gly Ser Gly Ala Gly Ala Gly Ser Gly Ala Gly
    1025            1030                1035

Ala Gly Ser Gly Ala Gly Ala Gly Ser Gly Ala Gly Ala Gly Ser
    1040            1045                1050

Gly Ala Gly Ala Gly Ser Gly Ala Gly Ala Gly Ser Gly Ala Gly
    1055            1060                1065

Ala Gly Ser Gly Ala Gly Ala Gly Ser Gly Ala Gly Ala Gly Ser
    1070            1075                1080

Gly Lys Gly Val Pro Gly Lys Gly Val Pro Gly Ala Gly Ala Gly
    1085            1090                1095

Ser Gly Ala Gly Ala Gly Ser Gly Ala Gly Ala Gly Ser Gly Ala
    1100            1105                1110

Gly Ala Gly Ser Gly Ala Gly Ala Gly Ser Gly Ala Gly Ala Gly
    1115            1120                1125

Ser Gly Ala Gly Ala Gly Ser Gly Ala Gly Ala Gly Ser Gly Ala
    1130            1135                1140

Gly Ala Gly Ser Gly Ala Gly Ala Gly Ser Gly Lys Gly Val Pro
    1145            1150                1155

Gly Lys Gly Val Pro Gly Ala Gly Ala Gly Ser Gly Ala Gly Ala
    1160            1165                1170

Gly Ser Gly Ala Gly Ala Gly Ser Gly Ala Gly Ala Gly Ser Gly
    1175            1180                1185

Ala Gly Ala Gly Ser Gly Ala Gly Ala Gly Ser Gly Ala Gly Ala
    1190            1195                1200

Gly Ser Gly Ala Gly Ala Gly Ser Gly Ala Gly Ala Gly Ser Gly
    1205            1210                1215

Ala Gly Ala Gly Ser Gly Lys Gly Val Pro Gly Lys Gly Val Pro
    1220            1225                1230

Gly Ala Gly Ala Gly Ser Gly Ala Gly Ala Gly Ser Gly Ala Gly
    1235            1240                1245

Ala Gly Ser Gly Ala Gly Ala Gly Ser Gly Ala Gly Ala Gly Ser
    1250            1255                1260

```
Gly Ala Gly Ala Gly Ser Gly Ala Gly Ala Gly Ser Gly Ala Gly
1265                1270                1275

Ala Gly Ser Gly Ala Gly Ala Gly Ser Gly Ala Gly Ala Gly Ser
        1280                1285                1290

Gly Lys Gly Val Pro Gly Lys Gly Val Pro Gly Ala Gly Ala Gly
1295                1300                1305

Ser Gly Ala Gly Ala Gly Ser Gly Ala Gly Ala Gly Ser Gly Ala
1310                1315                1320

Gly Ala Gly Ser Gly Ala Gly Ala Gly Ser Gly Ala Gly Ala Gly
1325                1330                1335

Ser Gly Ala Gly Ala Gly Ser Gly Ala Gly Ala Gly Ser Gly Ala
1340                1345                1350

Gly Ala Gly Ser Gly Ala Gly Ala Gly Ser Gly Lys Gly Val Pro
1355                1360                1365

Gly Lys Gly Val Pro Gly Ala Gly Ala Gly Ser Gly Ala Gly Ala
1370                1375                1380

Gly Ser Gly Ala Gly Ala Gly Ser Gly Ala Gly Ala Gly Ser Gly
1385                1390                1395

Ala Gly Ala Gly Ser Gly Ala Gly Ala Gly Ser Gly Ala Gly Ala
1400                1405                1410

Gly Ser Gly Ala Gly Ala Gly Ser Gly Ala Gly Ala Gly Ser Gly
1415                1420                1425

Ala Gly Ala Gly Ser Gly Lys Gly Val Pro Gly Lys Gly Val Pro
1430                1435                1440

Gly Ala Gly Ala Gly Ser Gly Ala Gly Ala Gly Ser Gly Ala Gly
1445                1450                1455

Ala Gly Ser Gly Ala Gly Ala Gly Ser Gly Ala Gly Ala Gly Ser
        1460                1465                1470

Gly Ala Gly Ala Gly Ser Gly Ala Gly Ala Gly Ser Gly Ala Gly
1475                1480                1485

Ala Gly Ser Gly Ala Gly Ala Gly Ser Gly Ala Gly Ala Gly Ser
        1490                1495                1500

Gly Lys Gly Val Pro Gly Lys Gly Val Pro Gly Ala Gly Ala Met
1505                1510                1515

Asp Pro Gly Arg Tyr Gln Asp Leu Arg Ser His His His His His
1520                1525                1530

His
```

US 11,648,279 B2

COMPOSITION FOR CELL TRANSPLANT, AND METHOD FOR CELL TRANSPLANT

TECHNICAL FIELD

The present invention relates to compositions for cell transplant and methods for cell transplant.

BACKGROUND ART

Regenerative medicine has been attracting an attention as a therapy for curing cardiac failures such as myocardial infarction. Regenerative medicine techniques aim to restore the functions of tissues or organs damaged by injury or disease by transplanting cells or the like, and have a potential to be an only therapy for cases hardly curative by current techniques. Adult cardiac myocytes are significantly poor in self-renewal potential, which causes great difficulty in restoring myocardial tissues when they are damaged. For restoring damaged myocardial tissues, an attempt has been made which includes transplanting a graft or a myocardium sheet containing myocardium cells in a damaged site by a cell technological method (Patent Literature 1). Such a method unfortunately tends to result in poor engraftment in the transplant site. Another attempt has been made as a cell transplant therapy which includes transplanting single cells, such as bone-marrow-derived mononuclear cells, skeletal-muscle-derived cells, adipose-tissue-derived stem cells, or myocardium bud cells taken from a myocardium in a myocardial tissue, with a syringe or through coronary artery (Non-Patent Literature 1). Such a method unfortunately results in that most transplanted cells fail in engraftment in the myocardial tissue. Transplanting cells alone reduces the persistence of transplanted cells in a damaged site. Thus, many studies have been made recently for transplanting cells along with a foundation material (matrix) that can improve the persistence. For example, hydrogel containing a predetermined cell growth factor is known as a therapeutic material for cell transplant applicable to cell transplant therapies using stem cells or the like (Patent Literature 2). The hydrogel has excellent biocompatibility, can improve the persistence of transplanted cells in a site having insufficient oxygen and nutrient supply.

The therapeutic material for cell transplant disclosed in Patent Literature 1 is prepared using as hydrogel an animal-derived material such as gelatin, which may cause infection or contamination of a transplant site by an animal-derived allergen substance possibly acting as a cause of immune response or by other impurities. Also, the persistence of transplanted cells in a transplant site and the proliferation, of cells are required to be improved.

CITATION LIST

Patent Literature

Patent: Literature 1: JP 2007-528755 T
Patent Literature 2: JP 2002-145797 A

Non-Patent Literature

Non-Patent Literature 1: Suzuki K et al., Circulation. 2004 Sep. 14; 110 (11 Suppl 1): II 225-30

SUMMARY OF INVENTION

Technical Problem

The present invention aims to provide a composition for cell transplant and a method for cell transplant, both of which enable a myocardial tissue to favorably retain cardiac myocytes and/or cardiac progenitors and can improve the persistence and proliferation of transplanted cells.

Solution to Problem

The inventors made intensive studies to arrive at the present invention.

Specifically, the present invention relates to a composition for cell transplant, containing cells and an aqueous solution containing a protein (A), the cells including a cardiac myocyte and/or a cardiac progenitor, the protein (A) having a degree of hydrophobicity of 0.2 to 1.2, the protein (A) containing a polypeptide chain (Y) and/or a polypeptide chain (Y'), the protein (A) containing 1 to 100 polypeptide chains as a total of the polypeptide chain (Y) and the polypeptide chain (Y'), the polypeptide chain (Y) being a polypeptide chain having 2 to 100 continuous amino acid sequences (X), the amino acid sequence (X) having any one of a VPGVG sequence (1) corresponding to an amino acid sequence of SEQ ID NO: 1, a GVGVP sequence (2) corresponding to an amino acid sequence of SEQ ID NO: 2, a GPP sequence, a GAP sequence, and a GAHGPAGPK sequence (3) corresponding to an amino acid sequence of SEQ ID NO: 3, the polypeptide chain (Y') being a polypeptide chain having a structure in which 0.1 to 5% amino acid residues in the polypeptide chain (Y) are replaced by a lysine residue and/or an arginine residue and including 1 to 100 residues as a total of the lysine residue and the arginine residue; and a method for cell transplant, including transplanting the composition for cell transplant of the present invention in a myocardial tissue of a mammal other than human.

Advantageous Effects of Invention

Transplanting cardiac myocytes and/or cardiac progenitors in a myocardial tissue using the composition for cell transplant and the method for cell transplant of the present invention enables the myocardial tissue to favorably retain the cardiac myocytes and/or cardiac progenitors. Furthermore, the persistence and proliferation of transplanted cells can be improved.

DESCRIPTION OF EMBODIMENTS

The composition for cell transplant of the present invention is a composition for cell transplant, containing cells and an aqueous solution containing a protein (A), the cells including a cardiac myocyte and/or a cardiac progenitor, the protein (A) having a degree of hydrophobicity of 0.2 to 1.2, the protein (A) containing a polypeptide chain (Y) and/or a polypeptide chain (Y'), the protein (A) containing 1 to 100 polypeptide chains as a 2' total of the polypeptide chain (Y) and the polypeptide chain (Y'), the polypeptide chain (1) being a polypeptide chain having 2 to 100 continuous amino acid sequences (X), the amino acid sequence (X) having any one of a VPGVG sequence (1) corresponding to an amino acid sequence of SEQ ID NO: 1, a GVGVP sequence (2) corresponding to an amino acid sequence of SEQ ID NO: 2, a PP sequence, a GAP sequence, and a GAHGPAGPK sequence (3) corresponding to an amino acid sequence of SEQ ID NO: 3, the polypeptide chain (Y') being a polypeptide chain having a structure in which 0.1 to 5% amino acid residues in the polypeptide chain (Y) are replaced by a lysine residue and/or an arginine residue and including 1 to 100 residues as a total of the lysine residue and the arginine residue.

Hereinafter, the structure of the composition for cell transplant of the present invention is described.

(Aqueous Solution Containing Protein (A))

The protein (A) is obtainable by extraction from a natural product, organic synthesis (e.g., enzyme method, solid phase synthesis, and liquid phase synthesis), genetic recombination, or the like. Organic synthesis can be performed according to a method disclosed in "Biochemical Experimental Course 1, Chemistry of Proteins IV (Seikagaku Jikken Mouza 1, Tanpakushitsu no Kagaku IV) (1981. 7. 1, edited by The Japanese Biochemical Society, published by Tokyo Kagaku Dozin. Co., Ltd.)" or a method disclosed in "Biochemical Experimental Course 2, Chemistry of Proteins (second volume) (Zoku Seikagaku Jikken Kouza 2, Tanpakushitsu no Kagaku (Ge)) (1987. 5. 20, edited by The Japanese Biochemical Society, published by Tokyo Kagaku Dozin Co., Ltd.)". Genetic recombination can be performed according to a method disclosed in JP 3338441 T or the like. The protein (A) can be obtained by any of extraction from a natural product, organic synthesis, and genetic recombination. Still, preferred is genetic recombination in terms of easiness in changing an amino acid sequence and inexpensive mass production.

Specifically, the polypeptide chain (Y) in the present invention includes a $(VPGVG)_b$ sequence (SEQ ID NO:1), a $(GVGVP)_c$ sequence (SEQ ID NO: 2), a $(GPP)_d$ sequence, a $(GAP)_e$ sequence, and a $(GAHGPAGPK)_f$ sequence (SEQ ID NO:3). (The letters b to f each represent the number of continuous amino acid sequences (X) and are each an integer of 2 to 100).

When one molecule of the protein (A) contains multiple polypeptide chains (Y), the polypeptide chains (Y) may have one kind or two or more kinds of sequences selected from the group consisting of the $(VPGVG)_b$ sequence (SEQ ID NO:1), the $(GVGVP)_c$ sequence (SEQ ID NO:2), the $(GPP)_d$ sequence, the $(GAP)_e$ sequence, and the $(CAHGPAGPK)_f$ sequence (SEQ ID NO:3).

When the protein (A) contains multiple polypeptide chains (Y) having amino acid sequences (X) of the same kind, the polypeptide chains (Y) may have the same or different number of continuous amino acid sequences (X). In other words, the protein (A) may contain polypeptide chains (Y) having the same number for a letter selected from b to f or may contain polypeptide chains (Y) having different numbers for a letter selected from b to f, i.e., different numbers of continuous amino acid sequences (X).

The amino acid sequence (X) constituting the polypeptide chain (Y) preferably has the VPGVG sequence (1) and/or the GVGVP sequence (2) in terms of the persistence and proliferation of cardiac myocytes and/or cardiac progenitors (hereinafter, collectively referred to as "cardiac myocytes or the like" when these need no particular distinguishment). In other words, the polypeptide chain (Y) preferably has the $(VPGVG)_b$ sequence (SEQ ID NO:1) and/or the $(GVGVP)_c$ sequence (SEQ ID NO:2) in terms of the persistence of cardiac myocytes or the like. When the protein (A) contains polypeptide chains (Y) having different kinds of amino acid sequences (X), the polypeptide chains (Y) preferably have two or more kinds of sequences selected from the group consisting of the $(GPP)_d$ sequence, the $(GVGVP)_e$ sequence (SEQ ID NO:2), and the $(GAHGPAGPK)_f$ sequence (SEQ ID NO:3), particularly preferably have the $(GVGVP)_e$ sequence (SEQ ID NO:2) and the $(GAHGPAGPK)_f$ sequence (SEQ ID NO:3) in terms of the persistence and proliferation of cardiac myocytes or the like.

The polypeptide chain (Y) is a polypeptide chain having 2 to 100 continuous amino acid sequences (X) (each of the letters b to f is 2 to 100). In terms of the persistence and proliferation of cardiac myocytes or the like, the number of continuous sequences is preferably 2 to 50 (each of the letters b to f is 2 to 50), more preferably 2 to 30 (each of the letters b to f is 2 to 30).

The polypeptide chain (Y') in the present invention is a polypeptide chain having a structure in which 0.1 to 5% amino acid residues in the polypeptide chain (Y) are replaced by a lysine residue (K) and/or an arginine residue (R) and having 1 to 100 residues as a total of the lysine residue and the arginine residue. Specifically, the polypeptide chain (Y') is a polypeptide chain in which part or the whole of the amino acid sequence (X) constituting the polypeptide chain (Y) is replaced by the following amino acid sequence (X') and 1 to 100 amino acid residues in the polypeptide chain (Y) are replaced by a lysine residue (K) and/or an arginine residue (R).

Amino acid sequence (X'): an amino acid sequence in which 20 to 60% amino acid residues in the amino acid sequence. (X) is replaced by a lysine residue (K) and/or an arginine residue (R).

In the amino acid sequence (X'), the number of amino acid residues in the amino acid sequence (X) replaced (the number replaced by a lysine residue (K) and/or an arginine residue (R)) is preferably 1 to 5, more preferably 1 to 4, still more preferably 0.1 to 3 in terms of the solubility of the protein (A) in water.

The amino acid sequence (X') includes preferably at least one kind of sequence selected from the group consisting of a GKGVP sequence (7) corresponding to an amino acid sequence of SEQ ID NO: 7, a GKGKP sequence (8) corresponding to an amino acid sequence of SEQ ID NO: 8, a GKGRP sequence (5) corresponding to an amino acid sequence of SEQ ID NO: 9, and a GRGRP sequence (10) corresponding to an amino acid sequence of SEQ ID NO: 10, more preferably at least one kind of sequence selected from the group consisting of the GKGVP sequence (7) (SEQ ID NO:7) and the GKGKP sequence (8) (SEQ ID NO:8) in terms of the solubility of the protein (A) in water.

Whether a polypeptide chain is the polypeptide chain (Y') or not is determined by replacing every K and R in the sequences of the protein (A) by a different amino acid residue (G, A, V, P, or H) and checking if the resultant polypeptide chain is the polypeptide chain (Y) or not. When the amino acid sequence (X) is the GAHGPAGPK sequence (3) (SEQ ID NO:3) that includes K, the determination method is changed as follows. That is, in the replacement of every K and R in the sequences of the protein (A) by a different amino acid residue (G, A, V, P, or H), when a GAHGPAGPα sequence appears (α represents G, A, V, P, or H), α is further replaced by K (SEQ ID NO:3). When the sequence becomes the polypeptide chain (Y) as a result of the replacement, the sequence before the replacement of amino acid residues is considered to be the polypeptide chain (Y'). In the polypeptide chain (Y'), the number of amino acid residues in the polypeptide chain (Y) replaced is preferably 1 to 70, more preferably 1 to 30 in terms of the solubility of the protein (A) in water and the persistence of the cardiac myocytes or the like. The polypeptide chain (Y') is a polypeptide chain having a structure in which 0.1 to 5% amino acid residues in the polypeptide chain (Y) are replaced by a lysine residue (K) and/or an arginine residue (R). The proportion is preferably 0.1 to 4%, more preferably 0.5 to 3% in terms of the solubility of the protein (A) in water and the persistence and proliferation of cardiac myocytes or the like.

The protein (A) in the present invention contains a polypeptide chain (Y) and/or a polypeptide chain (Y'), and the protein (A) contains 1 to 100 polypeptide chains as a total of the polypeptide chain (Y) and the polypeptide chain (Y'). When the protein (A) contains polypeptide chains (Y) having different kinds of amino acid sequence (X) and/or different numbers of continuous sequences, each polypeptide chain (Y) is counted as one and the number of polypeptide chains (Y) corresponds to the total number of polypeptide chains (Y). The same shall apply to the polypeptide chain (Y').

One molecule of the protein (A) contains 1 to 100 polypeptide chains as a total of the polypeptide chain (Y) and the polypeptide chain (Y'). The number is preferably 1 to 80, particularly preferably 1 to 60 in terms of the persistence and proliferation of cardiac myocytes or the like.

In the protein (A), one polypeptide chain (Y) corresponds to a portion where amino acid sequences (X) of the same kind are repetitively bonded and it continues until a point bonded to a sequence different from the amino acid sequence (X). For example, in a (GVGVP)$_{100}$GAGAGS (VPGVG)$_{20}$ sequence ((SEQ ID NO: 2)$_{100}$SEQ ID NO:4 (SEQ ID NO:1)$_{20}$), the polypeptide chain (Y) has two sequences: (GVGVP)$_{100}$ ((SEQ ID NO:2)$_{100}$) and (VPGVG). ((SEQ ID NO:1)$_{20}$). Similarly, one polypeptide chain (Y') corresponds to a portion where amino acid sequences (X) of the same kind are repetitively bonded and it continues until a point bonded to a sequence different from the amino acid sequence (X), wherein every lysine residue (K) and arginine residue (P) in the sequences of the protein (A) is replaced by a different amino acid (G, A, V, P, or H). For example, a (GVGVP)$_4$GKGVP(GVGVP)$_3$GAGAGS(GVGVP)$_4$GKGVP(GVGVP)$_3$ sequence ((SEQ ID NO:2)$_4$ SEQ ID NO:7 (SEQ ID NO:2)$_3$ SEQ ID NO:4 (SEQ ID NO:2)$_4$ SEQ ID NO:7 (SEQ ID NO:2)$_3$) includes two polypeptide chains (Y') both being (GVGVP)$_4$GKGVP(GVGVP) (SEQ ID NO:6).

The protein (A) in the present invention has a degree of hydrophobicity of 0.2 to 1.2. The degree of hydrophobicity is preferably 0.3 to 1.2, more preferably 0.4 to 1.2, still more preferably 0.45 to 1.2, particularly preferably 0.60 to 1.2, most preferably 0.60 to 0.75 in terms of the solubility of the protein (A) in water and in terms of gelation. The degree of hydrophobicity of the protein (A) shows the degree of hydrophobicity of molecules of the protein (A) and can be calculated according to the following formula by assigning the number (Mα) of amino acid residues of each kind constituting one molecule of the protein (A), the degree of hydrophobicity (Nα) of each amino acid, and the total number (MT) of amino acid residues in one molecule of the protein (A). For the degree of hydrophobicity of amino acids, the following values disclosed in Non-Patent Literature (Albert. L. Lehninger, David. L. Nelson, Lehninger principles of biochemistry, First volume, Hirokawa-Shoten Ltd., 2010. 9, p. 346-347) are used.

Degree of hydrophobicity=$\Sigma(M\alpha \times N\alpha)/(MT)$

Mα: number of amino acid residues of each kind in one molecule of protein (A)
Nα: degree of hydrophobicity of each amino acid
MT: total number of amino acid residues in one molecule of protein (A)
A (alanine): 1.8
R (arginine): −4.5
N (asparagine): −3.5
D (asparagine acid): −3.5
C (cysteine): 2.5
Q (glutamine): −3.5
E (glutamic acid): −3.5
G (glycine): −0.4
H (histidine): −3.2
I (isoleucine): 4.5
L (leucine): 3.8
K (lysine): −3.9
M (methionine): 1.9
F (phenylalanine): 2.8
P (praline): −1.6
S (serine): −0.8
T (threonine): −0.7
W (tryptophan): −0.9
Y (tyrosine): −1.3
V (valine): 4.2

For example, when the protein (A) has a (GVGVP)$_4$GKGVP (GVGVP)$_3$ sequence (6) corresponding to an amino acid sequence of SEQ ID NO: 6, the degree of hydrophobicity of the protein (A) is: degree of hydrophobicity of protein (A)={16 (number of Gs)×(−0.4)+15 (number of Vs)×4.2+8 (number of Ps)×(−1.6)+1 (number of Ks)×(−3.9)}/40 (total number of amino acid residues)=1.0.

The protein (A) in the present invention preferably further has the GAGAGS sequence (4) (SEQ ID NO:4). A protein (A) having the GAGAGS sequence (4) (SEQ ID NO:4) is further less likely to be intravitally degraded, which tends to allow the protein (A) to survive without being degraded until cardiac myocytes or the like are sufficiently engrafted in a myocardial tissue. The protein (A) preferably contains a polypeptide chain (5) having 2 to 100 continuous GAGAGS sequences (4) corresponding to an amino acid sequence of SEQ 1D NO: 4 in terms of biodegradation resistance. In the polypeptide chain (S), the number of continuous GAGAGS sequences (4) (SEQ ID NO:6) is preferably 2 to 100, more preferably 2 to 50, still more preferably 3 to 40, particularly preferably 4 to 30 in terms of biodegradation resistance. The protein (A), when containing the polypeptide chain (5), may contain at least one polypeptide chain (S) in one molecule. Still, the number of polypeptide chains (S) is preferably 1 to 20, more preferably 3 to 10 in terms of biodegradation resistance.

When the protein (A) contains two or more polypeptide chains as a total of the polypeptide chain (Y), the polypeptide chain (Y'), and the polypeptide chain (S), the protein (A) may have an intervening amino acid sequence (Z) between polypeptide chains. The intervening amino acid sequence (Z) is an amino acid sequence including one amino acid or two or more amino acids bonded to each other and being other than the polypeptide chain (Y), polypeptide chain (Y'), and polypeptide chain (S). The number of amino acids constituting the intervening amino acid sequence (Z) is preferably 1 to 30, more preferably 1 to 15, particularly preferably 1 to 10 in terms of biodegradation resistance. Specific examples of the intervening amino acid sequence (Z) include a VAAGY sequence (11) corresponding to an amino acid sequence of SEQ ID NO: 11, a GAAGY sequence (12) corresponding to an amino acid sequence of SEQ ID NO: 12, and a LGP sequence.

The protein (A) may include a terminal amino acid sequence (T) at the N- and/or C-terminus of any of the polypeptide chain (Y), polypeptide chain (Y'), and polypeptide chain (S) located at each terminus of the protein (A). The terminal amino acid sequence (T) is an amino acid sequence including one amino acid or two or more amino acids bonded to each other and being other than the polypeptide chain (Y), polypeptide chain (Y'), and polypeptide chain (S). The number of amino acids constituting the terminal amino acid sequence (T) is preferably 1 to 100, more preferably 1 to 50, particularly preferably 1 to 40 in terms of biodegradation resistance. Specific examples of the terminal amino acid sequence (T) include a MDPVVLQRRDWENPGVTQLNRLAAHPPFASDPM sequence (13) corresponding to an amino acid sequence of SEQ ID NO: 13.

The protein (A) may contain, in addition to the terminal amino acid sequence (T), a protein or peptide having a special amino acid sequence (hereinafter, these are collectively referred to as a "purification tag") at the N- and/or C-terminus of the protein (A) in order to achieve easy purification or detection of the expressed protein (A). For the purification tag, a tag for affinity purification is used. Examples of such a purification tag include glutathione-S-transferase (CTS), maltose binding protein (MBP), HQ tag, Myc tag, HA tag, FLAG tag, 6×His tag formed from polyhistidine, V5 tag, Xpress tag, AU1 tag, Ti tag, VSV-G tag, DDDDK tag, S tag, Cruz Tag 09TM, Cruz Tag 22TM, Cruz Tag 41TM, Glu-Glu tag, Ha.11 tag, and KT3 tag.

Following are combination examples of purification tag (i) and ligand (ii) for recognizing and binding the tag.
(i-1) glutathione-S-transferase (GTS) (ii-1) glutathione
(i-2) maltose binding protein (MBP) (ii-2) amylose
(i-3) HQ tag (ii-3) nickel.
(i-4) Myc tag (ii-4) anti-Myc antibody
(i-5) HA tag (ii-5) anti-HA antibody
(i-6) FLAG tag (ii-6) anti-FLAG antibody
(i-7) 6×His tag (ii-7) nickel or cobalt The purification tag sequence can be introduced by a method such as a method for inserting a nucleic acid encoding d purification tag at the 5'- or 3'-terminus of a nucleic acid encoding the protein (A) in an expression vector or a method of using a commercially available vector for introducing a purification tag.

One molecule of the protein (A) contains the polypeptide chain (Y) and the polypeptide chain (Y') in a total amount (wt %) of preferably 10 to 90 wt %, more preferably 20 to 00 wt % based on the molecular mass of the protein (A) in terms of interaction with cardiac myocytes or the like and in terms of the persistence and proliferation of cardiac myocytes or the like.

The total amount of the polypeptide chain (Y) and the polypeptide chain (Y') in the protein (A) can be determined by amino acid sequencing. Specifically, the following determination method is applicable.

<Method for Determining Total Amount of Polypeptide Chain (Y) and Polypeptide Chain (Y')>

Amino acid sequencing is performed with peptide sequencer (protein sequencer) PPSQ-33A available from Shimadzu Corporation. From the determined amino acid sequence, the total amount of the polypeptide chain (Y) and the polypeptide chain (Y') is calculated according to the following formula (1).

$$\text{Total amount of polypeptide chain } (Y) \text{ and polypeptide chain } (Y') = \Sigma(\gamma \times \beta)/\Sigma(\alpha \times \beta) \times 100 \quad (1)$$

α: number of amino acid residues of each kind in protein (A)
β: molecular mass of each amino acid
γ: number of amino acids of each kind in polypeptide chain (Y) and polypeptide chain (Y')

One molecule of the protein (A) contains the amino acid sequence (X) and the amino acid sequence (X') in a total amount (wt %) of preferably 10 to 90 wt %, more preferably 20 to 80 wt % based on the molecular mass of the protein (A) in terms of the persistence and proliferation of cardiac myocytes or the like.

The total amount of the amino acid sequence (X) and the amino acid sequence (X') in the protein (A) can be determined with a protein sequencer. Specifically, the following method is applicable.

<Method for Determining Amount of Amino Acid Sequence (X) and Amino Acid Sequence (X')>

The protein (A) is degraded into about 30 residues or less using two or more methods selected from methods for cutting a protein with a specific amino acid residue. The fragments of the protein (A) are separated by high-performance liquid chromatography (HPLC), and then the amino acid sequences of the fragments are read with a protein sequencer. The obtained amino acid sequences of the fragments are subjected to peptide mapping, whereby all sequences of the protein (A) are determined. Thereafter, the total amount of the amino acid sequence (X) and the amino acid sequence (X') is calculated according to the following determination formula.

$$\text{Total amount (\%) of amino acid sequence } (X) \text{ and amino acid sequence } (X') = [\{\text{molecular mass of amino acid sequence } (X)\} \times \{\text{number of amino acid sequences } (X)\} + \{\text{molecular mass of amino acid sequence } (X')\} \times \{\text{number of amino acid sequences } (X')\}]/\{\text{molecular mass of protein } (A)\} \times 100$$

One molecule of the protein (A) has a ratio in the number of sequences of the GAGAGS sequence (4) (SEQ ID NO: 4) to the total of the amino acid sequence (X) and the amino acid sequence (X') (GAGAGS sequence (4) (SEQ ID NO: 4):total of amino acid sequence (X) and amino acid sequence (X')) of preferably 4:1 to 1:20, more preferably 4:1 to 1:10 in terms of the solubility of the protein (A) in water and the persistence and proliferation of cardiac myocytes or the like.

The protein (A) has a molecular mass of preferably 15 to 200 kDa, more preferably 15 to 100 kDa in terms of the persistence and proliferation of cardiac myocytes or the like. The molecular mass of the protein (A) can be determined by separating a measurement sample and comparing the migration distance thereof with that of a reference material by the SOS polyacrylamide gel electrophoresis (SUS-PAGE) method.

Preferred examples of the protein (A) include the following.

(1) Protein Having GVGVP Sequence (2) as Amino Acid Sequence (X)

(1-1) Preferred is a protein (A1) containing a polypeptide chain (Y'1) having a structure in which one amino acid residue in a polypeptide chain (Y1) having continuous GVGVP sequences (2) (SEQ ID NO:2) is replaced by a lysine residue (K). More preferred are a protein (A2) containing a polypeptide chain (Y'2) having a (GVGVP)$_4$GKGVP(GVGVP)$_3$ sequence (6) (SEQ ID NO:6) and a polypeptide chain (S1) having a (GAGAGS)$_4$ sequence (5) (SEQ ID NO:5); a protein (A4) containing a polypeptide chain (Y'2) and a polypeptide chain (S2) having a (GAGAGS)$_2$ sequence (14); and a protein (A5) containing a polypeptide chain (Y'2), a polypeptide chain (S1), and a polypeptide chain (S2). A specific example is a protein (SELP8K, degree of hydrophobicity 0.62) having a molecular mass of about 80 kDa and having a sequence (15) corresponding to an amino acid sequence of SEQ ID NO: 15. This protein contains 12 polypeptide chains (S1), each of which has a (GAGAGS)$_4$ sequence (5) consisting of four continuous GAGAGS sequences (4), and 13 polypeptide chains (Y'2), each of which has a (GVGVP)$_4$GKGVP (GVGVP)$_3$ sequence (6) (SEQ ID NO:6) having a structure in which one of valine residues (V) in a polypeptide chain (Y2) consisting of eight continuous GVGVP sequences (2) (SEQ ID NO:2) is replaced by a lysine residue (K). To a structure with these polypeptide chains alternately chemically bonded, one polypeptide chain (S2) is bonded which has a (GAGAGS)$_2$ sequence (14) (SEQ ID NO:14) consisting of two continuous GAGAGS sequences (4) (SEQ ID NO:4). Another specific example is a protein (SELP0K, degree of hydrophobicity 0.72) having a molecular mass of about 82 kDa and having a sequence (16) corresponding to an amino acid sequence of SEQ ID NO: 16. This protein contains 17 polypeptide chains (S2) having a (GAGAGS)$_2$ sequence (14) (SEQ ID NO:14) consisting of two continuous GAGAGS sequences (4) (SEQ ID NO:4) and 17 polypeptide chains (Y'2) having a (GVGVP)$_4$GKGVP (GVGVP)$_3$ sequence (6) (SEQ ID NO:6). These polypeptide chains are alternately chemically bonded.

(1-2) Preferred is a protein (A6) containing a polypeptide chain (Y1) that has continuous GVGVP sequences (2). More preferred is a protein (A7) containing a polypeptide chain (Y1) consisting of two continuous GVGVP sequences (2) (SEQ ID NO:2) and a polypeptide chain (S3) consisting of six continuous GAGAGS sequences (4) (SEQ ID NO:4). A specific example is a protein (SLP4.1, degree of hydrophobicity 0.47) having a molecular mass of about. 93 kDa and having a sequence (17) corresponding to an amino acid sequence of SEQ ID NO: 17. This protein contains 29 amino acid blocks (L-1) which are repetitively chemically bonded and each of which contains a polypeptide chain (Y1) and a polypeptide chain (S3) bonded to each other.

(2) Protein Having VPGVG Sequence (1) (SEQ ID NO:1) as Amino Acid Sequence (X)

(2-1) A preferred example is a protein (A8) containing a polypeptide chain (Y3) consisting of four continuous VPGVG sequences (1) and a polypeptide chain (Y4) consisting of eight continuous VPGVG sequences (1) (SEQ ID NO:1). A more preferred example is a protein (A9) containing a polypeptide chain (Y3) consisting of four continuous VPGVG sequences (1), a polypeptide chain (Y4) consisting of eight continuous VPGVG sequences (1) (SEQ ID NO:1), and a GAGAGS sequence (4) (SEQ ID NO:4). A specific example is a protein (ELP1.1, degree of hydrophobicity 1.12) having a molecular mass of about 220 kDa and having a sequence (18) corresponding to an amino acid sequence of SEQ ID NO: 18. This protein contains repetitively chemically bonded 40 amino acid blocks (L-2) each having a structure in which a polypeptide chain (Y3) is bonded to a GAGAGS sequence (4) (SEQ ID NO:4) and a polypeptide chain (Y4) is further bonded to the structure.

Also, the protein (A) may be a protein having a homology with a protein having the sequence (15), a protein having the sequence (16), a protein having the sequence (17), or a protein having the sequence (18).

The homology is preferably 80% or higher, more preferably 90% or higher, still more preferably 95% or higher.

Any water may be used for the aqueous solution containing the protein (A), but preferred is sterilized water. Examples include those sterilized by various methods, such as water having passed through a microfiltration membrane having a pore diameter of 0.2 μm or smaller, water having passed through an ultrafiltration membrane, water having passed through a reverse osmosis membrane, and ion-exchange water after heat sterilization by heating at 121° C. for 20 minutes in an autoclave.

(Cells)

As described above, the composition for cell transplant of the present invention can improve the persistence and proliferation of cardiac myocytes and/or cardiac progenitors in a myocardium.

Examples of the cardiac progenitor include cells on whose surface a protein such as a neurturin receptor (GFRA2) protein, a platelet-derived growth factor receptor α (PDGFRA) protein, or a kinase insert domain protein receptor (KDR) protein is expressed.

The cardiac myocytes and/or cardiac progenitors are preferably derived from a mammal.

The cardiac myocytes and/or cardiac progenitors are also preferably derived from stem cells.

The stem cells may be stem cells isolated from a tissue or successively cultured stem cells. Any kind of stem cells may be used and examples thereof include mouse embryonic stem cells, mouse mesenchymal stem cells, mouse pluripotent stem cells, human embryonic stem cells, human mesenchymal stem cells, and human pluripotent stem cells. Preferred among these are human pluripotent stem cells in terms of handleability and safeness. In terms of immune rejection, a target for cell transplant is preferably a mammal, more preferably a human.

Stem cells may be differentiated into cardiac myocytes and/or cardiac progenitors by any method such as a method disclosed in (Funakoshi, S. et al., Sci Rep 8, 19111 (2016)) to provide cardiac myocytes and/or cardiac progenitors.

The composition for cell transplant of the present invention may not contain animal-derived serum or the like. Absence of animal-derived serum or the like can presumably reduce antigenicity.

The protein (A) contained in the composition for cell transplant of the present invention, including a biological sequence, presumably has high biocompatibility. Moreover, the protein (A) can be inexpensively mass-produced from bacteria such as *E. coli*, achieving easy production.

Furthermore, the protein (A) contained in the composition for cell transplant of the present invention is less likely to be degraded by internal proteases and is thus durable, achieving long-term intravital existence.

The composition for cell transplant of the present invention contains the protein (A) at a concentration of preferably 1 to 20 wt %, more preferably 2 to 20 wt %, still more preferably 10 to 20 wt % based on the total weight of the composition for cell transplant.

When the concentration of the protein (A) in the composition for cell transplant is 1 to 20 wt % based on the total weight of the composition for cell transplant, the composition for cell transplant has sufficiently high viscosity. Thereby, cardiac myocytes or the like can be favorably engrafted in a myocardial tissue, which improves the persistence of the cardiac myocytes or the like.

In particular, when the concentration of the protein (A) in the composition for cell transplant is 10 to 20 wt. % based on the total weight of the composition for cell transplant, the composition for cell transplant loses fluidity when heated to about 37° C. and results in gel with a certain hardness at which the gel does not lose its form by its own weight. Gelation of the composition for cell transplant can prevent dispersion of cardiac myocytes or the like, which can more improve the persistence of the cardiac myocytes or the like.

The gelation is achievable without adding a gelator such as a cross-linker to the composition for cell transplant. The gelation proceeds in the presence of the composition for cell transplant only. The composition for cell transplant of the present invention preferably contains no gelator such as a cross-linker.

The composition for cell transplant of the present invention contains cardiac myocytes and/or cardiac progenitors at a concentration of preferably $1\times10^5$ to $1\times10^3$ pcs/ml, based on the total fluid volume of the composition for cell transplant.

When the concentration of the cardiac myocytes or the like in the composition for cell transplant is lower than $1\times10^5$ pcs/mL based on the total fluid volume of the composition for cell transplant, the number of the cardiac myocytes or the like is too small, which unlikely achieves a sufficient effect of transplanting cells in a myocardial tissue.

When the concentration of the cardiac myocytes or the like in the composition for cell transplant is higher than $1\times10^3$ pcs/mL based on the total fluid volume of the composition for cell transplant, the number of the cardiac myocytes or the like is excessive, which tends to result in insufficient improvement in persistence of the cardiac myocytes or the like transplanted in a myocardium. Additionally, such a concentration is uneconomical in terms of cost efficiency.

(Different Component)

The composition for cell transplant of the present invention may further contain inorganic salt and phosphoric acid (salt).

Examples of the inorganic salt include sodium chloride, potassium chloride, calcium chloride, magnesium chloride, sodium sulfate, potassium sulfate, calcium sulfate, magnesium sulfate, sodium hydrogen carbonate, potassium hydrogen carbonate, calcium hydrogen carbonate, and magnesium hydrogen carbonate. Here, phosphates are not included in inorganic salt.

The composition for cell transplant of the present invention contains salt in an amount (wt %) of preferably 0 to 1.3 wt %, more preferably 0.5 to 1.3 wt %, still more preferably 0.7 to 1.1 wt %, particularly preferably 0.85 to 0.95 wt % based on the total weight of the composition for cell transplant in terms of the persistence and proliferation of cardiac myocytes or the like.

Phosphoric acid (salt) as used herein means phosphoric acid and/or phosphoric salt. Examples of the phosphoric acid (salt) contained in the composition for cell transplant of the present invention include phosphoric acid and phosphates. Examples of the salt include alkali metal salt and alkaline-earth metal salt. Specific examples thereof include sodium salt, potassium salt, calcium salt, and magnesium salt.

The composition for cell transplant of the present invention contains phosphoric acid (salt) in an amount (wt %) of preferably 0 to 0.30 wt %, more preferably 0.10 to 0.30 wt %, still more preferably 0.12 to 0.28 wt %, particularly preferably 0.14 to 0.26 wt % based on the total weight of the composition for cell transplant in terms of the solubility of the protein (A).

The composition for cell transplant may further contain a growth factor.

The type of the growth factor, when contained in the composition for cell transplant, is preferably selected according to the damaged site and the type of the target disease.

Examples of the growth factor include epidermal growth factors (EGF), insulin-like growth factors (IGF), transforming growth factors (TGF), nerve growth factors (NSF), brain-derived neurotrophic factors (BDNF), vesicular endothelial growth factors (VEGF), granulocyte-colony stimulating factors (G-CSF), granulocyte-macrophage-colony stimulating factors (GM-CSF), platelet-derived growth factors (PDGF), erythropoietin (EPO), thrombopoietin (TPO), basic fibroblast growth factors (bFGF or FGF2), and hepatocyte growth factors (HGF).

The composition for cell transplant contains a growth factor at a concentration of preferably 0.003 to 9.1 wt %, more preferably 0.003 to 6.25 wt % based on the total weight of the composition for cell transplant in terms of cell proliferation.

The composition for cell transplant may further contain known substances such as differentiated factors, hormones, chemokines, cytokines, cell adhesion molecules, chemotactic factors, enzymes, enzyme inhibitors, coenzymes, minerals, fats, lipids, sugars, antibiotics, inflammation inhibitors, immunosuppressants, buffering substances, stabilizers, and vitamins.

The composition for cell transplant has a pH of preferably 5 to 9, more preferably 6 to 8 in terms of tissue affinity. The pH can be adjusted by adding a substance such as a known buffering substance.

Next, usage of the composition for cell transplant of the present invention is described.

The composition for cell transplant of the present invention can be used for a cardiac myocyte transplant therapy.

In other words, a target tissue of the composition for cell transplant of the present invention is a myocardial tissue.

The composition for cell transplant of the present invention may be used for any disease, and examples thereof include myocardial infarction, angina pectoris, cardiomyopathy, and myocarditis.

In other words, an embodiment of the present invention is use of the composition for cell transplant of the present invention for a cardiac myocyte transplant therapy, and another embodiment of the present invention is use of the composition for cell transplant of the present invention for a cardiac myocyte transplant therapy in order to cure at least one disease selected from the group consisting of myocardial infarction, angina pectoris, cardiomyopathy, and myocarditis.

A method for transplant to myocardia using the composition for cell transplant of the present invention is described in the following.

The method for cell transplant of the present invention includes transplanting the composition for cell transplant of the present invention in a myocardial tissue of a mammal.

The mammal in the method for cell transplant of the present invention may be any mammal, and examples thereof include human, mouse, rat, pig, and monkey.

The number of cells to be transplanted in a myocardial tissue in the method for cell transplant of the present invention is preferably $1\times10^3$ to $1\times10^8$.

Less than $1\times10^3$ cells to be transplanted are too few, which unlikely achieves a sufficient effect of transplanting cells.

More than $1\times10^8$ cells to be transplanted are excessive, which tends to result in insufficient improvement in persistence of cells transplanted in a myocardium. Additionally, such an excessive number of cells are uneconomical in terms of cost efficiency.

EXAMPLES

Hereinafter, the present invention is specifically described with reference to examples and comparative examples, which do not intend to limit the present invention. Unless otherwise specified, % refers to wt % and part(s) refers to part(s) by weight in the following.

Production Example 1

Production of SELP8K

Plasmid pPT034.5 encoding SELP8K was produced in accordance with the method disclosed in an example of JP 4088341 B.

The plasmid was transformed into E. coli, and whereby a SELP8K producer strain was obtained.

A broth of the SELP8K producer strain cultured overnight at 30° C. was inoculated in a 50-ml LB medium in a 250-ml flask. Kanamycin was added to the flask such that the final concentration was 50 μg/ml. This broth was cultured at 30° C. while being stirred (200 rpm). When the broth satisfied OD600=0.8 (using absorption spectrometer UV1700 available from Shimadzu Corporation), the broth in an amount of 40 ml was moved to a flask warmed to 42° C. and cultured at the same temperature for about two hours. The culture was cooled with ice and then the OD600 of the broth was determined. E. coli was collected by centrifugation. The collected E. coli was lysed by ultrasonic grinding (4° C., 30 sec×10 times) in order to extract a protein from the collected E. coli.

The protein produced from E. coli was subjected to sodium dodecyl sulfate-polyacrylamide gel electrophoresis (SDS-PAGE) and was then transferred onto a polyvinylidene fluoride film. Thereafter, western blot analysis was performed using a rabbit anti-SELP8K antibody as a primary antibody and an anti-rabbit IgG HRP labeled antibody (available from GE Healthcare) as a secondary antibody. The product had an apparent molecular mass of about 80 kDa. This revealed that the SELP8K producer strain produced SELP8K having an apparent molecular mass of 80 kDa and having reactivity with a rabbit anti-SELP8K antibody.

Purification of SELP8K

The above-obtained SELP8K was purified from E. coli biomass by bacteriolysis, removal of insoluble debris by centrifugation, and affinity chromatography. Thereby, a protein (A-1) (SELP8K) having a molecular mass of about 80 kDa was obtained.

Identification of SELP8K.

The obtained protein (A-1) was identified by the following procedure.

The protein was analyzed by western blot using a rabbit anti-SELP8K antibody and a rabbit anti-6×His antibody (available from Roland) against a 6×His tag of a C-terminal sequence. A protein band having an apparent molecular mass of 80 kDa showed antibody reactivity with each antibody. The obtained protein was subjected to amino acid analysis, which demonstrated that the product was rich in glycine (43.7%), alanine (12.3%), serine (5.3%), proline (11.7%), and valine (21.2%). The product also contained lysine in an amount of 1.5%. The following Table 1 shows a correlation between the composition of the purified product and the composition by prediction theory from synthesized gene sequences.

Accordingly, the protein (A-1) was confirmed as a protein having a sequence (15). Specifically, the protein had a structure in which 13 (GVGVP)$_4$GKGVP (GVGVP) sequences (6) (SEQ ID NO:6) and 12 (GAGAGS)$_4$ sequences (5) (SEQ ID NO:5) were alternately chemically bonded, and a (GAGAGS)$_2$ sequence (14) (SEQ ID NO:14) was chemically bonded to the structure.

TABLE 1

| Amino acid | Actual determination Composition percentage (%) | Theoretical value Composition percentage (%) |
|---|---|---|
| Ala | 12.3 | 12.2 |
| Asx | 0.9 | 0.8 |
| Glx | n.d. | 0.4 |
| Phe | 0.4 | 0.1 |
| Gly | 43.7 | 41.5 |
| His | 0.4 | 0.8 |
| Ile | 0.3 | 0 |
| Lys | 1.5 | 1.5 |
| Leu | 0.3 | 0.5 |
| Met | 0.3 | 0.3 |
| Pro | 11.7 | 12.4 |
| Arg | 0.5 | 0.6 |
| Ser | 5.3 | 6.1 |
| Thr | n.d. | 0.1 |
| Val | 21.2 | 22.4 |
| Tyr | 1.1 | 0.1 |

Production Example 2

A protein (A-2) having a molecular mass of about 82 kDa and having a sequence (16) was obtained as in Production Example 1, except that. "plasmid pPT0364 encoding SELP0K" was used instead of "plasmid pPT0345 encoding SELP8K".

Production Example 3

A protein (A-3) having a molecular mass of about 93 kDa and having a sequence (17) was obtained as in Production Example 1, except that "pSY1398-1 encoding SLP4.1" was used instead of "plasmid pPT0345 encoding SELP8K".

Production Example 4

A protein (A-4) having a molecular mass of about 220 kDa and having a sequence (18) was obtained as in Production Example 1, except that "plasmid pPT0102-1 encoding ELP1.1" was used instead of "plasmid pPT0345 encoding SELP8K".

Comparative Production Example 1

A protein (A'-1) having a molecular mass of about 150 kDa and having a sequence (19) corresponding to an amino acid sequence of SEQ ID NO: 19 was obtained as in Production Example 1, except that "plasmid pPT102 encoding SLP4.1.3" was used instead of "plasmid pPT0345 encoding SELP8K".

<Method for Producing Cells for Transplant>

Human pluripotent stem cells constantly expressing luciferase were produced by inserting luciferase genes to a healthy human pluripotent stem cell strain using PiggyBac transposon vector system (available from System-Biosciences) with CAG promoter. From this cell strain, human pluripotent stem cells were differentiated and induced by a method disclosed in (Funakoshi, S. et al., Sci Rep 8, 19111 (2016)). On the 20th day from the differentiation and induction, cardiac myocytes were separately extracted by flow cytometry, whereby a solution containing cardiac myocytes for transplant was produced.

Example 1

The protein (A-1) and water were added to the solution containing cardiac myocytes for transplant such that the concentration of the protein (A-1) was 10 wt % and the concentration of the cardiac myocytes for transplant was 5×10$^7$ pcs/mL, whereby a composition for cell transplant of Example 1 was prepared.

Examples 2 to 4

Compositions for cell transplant of Examples 2 to 4 were prepared as in Example 1, except that the protein (A-2) to the protein (A-4) were used instead of the protein (A-1).

Comparative Example 1

Water was added to the solution containing cardiac myocytes for transplant such that the concentration of the cardiac myocytes for transplant was 5×10$^7$ pcs/mL, whereby a composition for cell transplant of. Comparative Example 1 was prepared.

Comparative Example 2

A composition for cell transplant of Comparative Example 2 was prepared as in Example 1, except that the protein (A'-1) was used instead of the protein (A-1).

<Transplant of Cardiac Myocytes to Mouse>

The composition for cell transplant of each of the examples and comparative examples in an amount of 20 (the number of cells 1×10$^6$) was injected with a syringe into a myocardial tissue of model mice having myocardial infarction. After one hour from the injection, luciferin was intraperitoneally administered to each mouse with a syringe, and the emission intensity of luciferase in the myocardial tissue of the mouse was detected using in vivo imaging system (IVIS).

<Evaluation for Persistence of Cardiac Myocytes after Cell Transplant (0th Day from Cell Transplant)>

The persistence of the cardiac myocytes on the 0th day from cell transplant was calculated according to the following formula using the detected emission intensity. The results are shown in Table 2.

(Persistence of cardiac myocytes on the 0th day from cell transplant)=(emission intensity of luciferase)/(emission intensity of luciferase in Comparative Example 1)

The "persistence of cardiac myocytes on 0th day from cell transplant (relative value)" in Table 2 shows relative ratios to the "luciferase emission intensity on 0th day from cell transplant" of a mouse injected with the composition for cell transplant of Comparative Example 1 defined as 1.0.

<Evaluation for Proliferation of Cardiac Myocytes after Cell Transplant (0th Day to 84th Day from Transplant)>

The mouse injected with the composition for cell transplant of each of the examples and comparative examples was raised, and luciferin was intraperitoneally administered with a syringe on the 3rd, 5th, 7th, 14th, 28th, 56th, and 84th days. The emission intensity of luciferase in the myocardial tissue of the mouse was detected using in vivo imaging system (IVIS).

The proliferation of cardiac myocytes after cell transplant was calculated according to the following formula using the detected emission intensity. The results are shown in Table 3.

(Proliferation of cardiac myocytes after cell transplant)=(emission intensity of luciferase)/(emission intensity of luciferase on 0th day from cell transplant)

The "proliferation of cardiac myocytes after cell transplant (relative value)" in Table 3 shows relative ratios to the "luciferase emission intensity on 0th day from cell transplant" of the mouse injected with the composition for cell transplant of the corresponding example or comparative example defined as 1.0.

TABLE 2

| | Type of protein (A) | | | Degree of hydrophobicity of protein (A) | Concentration of protein (A) (wt %) | Persistence of cardiac myocytes on 0th day from cell transplant (relative value) [relative ratio to Comparative Example 1 defined as 1.0] |
|---|---|---|---|---|---|---|
| Example 1 | Production Example 1 | A-1 | SELP8K | 0.62 | 10 | 10.2 |
| Example 2 | Production Example 2 | A-2 | SELP0K | 0.72 | 10 | 9.8 |
| Example 3 | Production Example 3 | A-3 | SLP4.1 | 0.47 | 10 | 9.5 |
| Example 4 | Production Example 4 | A-4 | ELP1.1 | 1.12 | 10 | 8.9 |
| Comparative Example 1 | — | — | — | — | 0 | 1.0 |
| Comparative Example 2 | Comparative Production Example 1 | A'-1 | SLP4.1.3 | 0.17 | 10 | 1.5 |

TABLE 3

| | Type of protein (A) | | | Degree of hydrophobicity of protein (A) | Concentration of protein (A) (wt %) | Proliferative property of cardiac myocytes after cell transplant (relative value) [relative ratio to emission intensity of luciferase on 0th day from cell transplant defined as 1.0] | | | | | | | |
|---|---|---|---|---|---|---|---|---|---|---|---|---|---|
| | | | | | | 0th day | 3rd day | 5th day | 7th day | 14th day | 28th day | 56th day | 84th day |
| Example 1 | Production Example 1 | A-1 | SELP8K | 0.82 | 10 | 1.0 | 0.8 | 1.5 | 2.0 | 2.6 | 4.9 | 5.7 | 8.1 |
| Example 2 | Production Example 2 | A-2 | SELP0K | 0.72 | 10 | 1.0 | 0.8 | 1.4 | 1.8 | 2.5 | 4.7 | 5.2 | 7.8 |
| Example 3 | Production Example 3 | A-3 | SLP4.1 | 0.47 | 10 | 1.0 | 0.7 | 1.3 | 1.7 | 2.3 | 4.5 | 5.0 | 8.0 |
| Example 4 | Production Example 4 | A-4 | ELP1.1 | 1.12 | 10 | 1.0 | 0.7 | 1.3 | 1.7 | 2.3 | 4.4 | 4.9 | 5.5 |
| Comparative Example 1 | — | — | — | — | 0 | 1.0 | 0.6 | 0.9 | 1.0 | 1.8 | 2.8 | 3.0 | 3.9 |
| Comparative Example 2 | Comparative Production Example 1 | A'-1 | SLP4.1.3 | 0.17 | 10 | 1.0 | 0.7 | 0.9 | 1.0 | 1.8 | 2.5 | 3.1 | 4.1 |

Table 2 demonstrates that the persistence of cardiac myocytes after cell transplant was evaluated as significantly better in use of the compositions for cell transplant of Examples 1 to 4 than in use of the compositions for cell transplant of Comparative Examples 1 and 2.

In addition, Table 3 demonstrates that the proliferation of cardiac myocytes after cell transplant was evaluated as better in use of the compositions for cell transplant of Examples 1 to 4 than in use of the compositions for cell transplant of Comparative Examples 1 and 2.

Accordingly, use of the composition for cell transplant of the present invention enables a myocardial tissue to retain cardiac myocytes and improves the proliferation of cells.

INDUSTRIAL APPLICABILITY

The composition for cell transplant and the method for cell transplant of the present invention enable a myocardial tissue to favorably retain cardiac myocytes or the like and can improve the persistence and proliferation of transplanted cells. Accordingly, the composition for cell transplant and the method for cell transplant of the present invention are effectively applicable to diseases characterized by insufficient cardiac functions, such as myocardial infarction.

The invention claimed is:

1. A composition for cell transplant, comprising cells and an aqueous solution containing a protein (A),
    the cells including a cardiac myocyte and/or a cardiac progenitor,
    the protein (A) having a degree of hydrophobicity of 0.2 to 1.2,
    the protein (A) containing a polypeptide chain (Y) and/or a polypeptide chain (Y'),
    the protein (A) containing 1 to 100 polypeptide chains as a total of the polypeptide chain (Y) and the polypeptide chain (Y'),
    the polypeptide chain (Y) being a polypeptide chain having 2 to 100 continuous amino acid sequences (X), the amino acid sequence (X) having any one of a VPGVG (SEQ ID NO: 1), a GVGVP (SEQ ID NO: 2), a GPP sequence, a GAP sequence, and a GAHGPAGPK (SEQ ID NO: 3),
    the polypeptide chain (Y') being a polypeptide chain having a structure in which 0.1 to 5% amino acid residues in the polypeptide chain (Y) are replaced by a lysine residue and/or an arginine residue and including 1 to 100 residues as a total of the lysine residue and the arginine residue,
    wherein the protein (A) is at least one protein selected from the group consisting of SELP8K protein (SEQ ID NO: 15), SELP0K protein (SEQ ID NO: 16), SLP4.1 protein (SEQ ID NO: 17), ELP 1.1 protein (SEQ ID NO: 18) and a protein having a homology being 80% or more with SELP8K protein, SELP0K protein, SLP4.1 protein or ELP 1.1 protein.

2. The composition for cell transplant according to claim 1,
    wherein the protein (A) is present at a concentration of 1 to 20 wt % based on a total weight of the composition for cell transplant.

3. The composition for cell transplant according to claim 1,
wherein the cells are present at a concentration of $1\times10^5$ to $1\times10^9$ pcs/mL based on a total fluid volume of the composition for cell transplant.

4. The composition for cell transplant according to claim 1,
wherein the cells are derived from a stem cell.

5. The composition for cell transplant according to claim 1,
wherein the cells are derived from a mammal.

6. The composition for cell transplant according to claim 1,
wherein the cells are derived from a human pluripotent stem cell.

7. A method for cell transplant, comprising transplanting the composition for cell transplant according to claim 1 in a myocardial tissue of a mammal other than human.

8. A method for cell transplant according to claim 7,
wherein $1\times10^3$ to $1\times10^8$ cells are transplanted in the myocardial tissue.

\* \* \* \* \*